United States Patent
Kitajima et al.

(10) Patent No.: US 11,308,181 B2
(45) Date of Patent: Apr. 19, 2022

(54) DETERMINATION METHOD AND DETERMINATION APPARATUS

(71) Applicant: FUJITSU LIMITED, Kawasaki (JP)

(72) Inventors: Hironobu Kitajima, Kawasaki (JP); Tetsuya Kashiwagi, Fukuoka (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 17/104,332

(22) Filed: Nov. 25, 2020

(65) Prior Publication Data
US 2021/0165851 A1    Jun. 3, 2021

(30) Foreign Application Priority Data
Nov. 28, 2019   (JP) .............................. JP2019-215133

(51) Int. Cl.
*G06F 17/15*    (2006.01)
*G16H 40/63*   (2018.01)

(52) U.S. Cl.
CPC ............. *G06F 17/15* (2013.01); *G16H 40/63* (2018.01)

(58) Field of Classification Search
CPC ........................ G06F 17/15–156; G01S 7/2926
See application file for complete search history.

(56) References Cited

U.S. PATENT DOCUMENTS

2018/0128861 A1 *   5/2018   Jang ..................... G01R 19/003
2019/0167200 A1     6/2019   Jang et al.

FOREIGN PATENT DOCUMENTS

| JP | 2005-066044 A | 3/2005 |
| JP | 2019-098183 A | 6/2019 |
| JP | 2019-159779 A | 9/2019 |

OTHER PUBLICATIONS

B. Boucheham, Reduced data similarity-based matching for time series patterns alignment, Pattern Recognition Letters, 31, 629-638, 2010 (Year: 2010).*

I. Boulnemour et al., QP-DTW: Upgrading Dynamic Time Warping to Handle Quasi Periodic Time Series Alignment, J. Inf. Process. Syst., vol. 14, No. 4 pp. 851-876, 2018 (Year: 2018).*

(Continued)

*Primary Examiner* — Emily E Larocque
(74) *Attorney, Agent, or Firm* — Fujitsu Patent Center

(57) ABSTRACT

A first time-series data set indicating first measured values obtained by a first device and a second time-series data set indicating second measured values obtained by a second device are obtained. First alignment is performed to convert the positions in the time domain of the first measured values belonging to a second period, based on the first measured values belonging to a first period. Second alignment is performed to convert the positions in the time domain of the second measured values belonging to the second period, based on a relationship between positions before and after the conversion. Correlation analysis is performed between third and fourth time-series data sets respectively obtained by the first and second alignment. The existence or absence of an inclusion relationship in which the second measured values contain a component of the first measured values is determined based on the correlation analysis result.

10 Claims, 19 Drawing Sheets

(56) References Cited

OTHER PUBLICATIONS

G. Ganeshapillai et al., Weighted Time Warping for Temporal Segmentation of Multi-Parameter Physiological Signals, Proceedings of the International Conference on Bio-inspired Systems and Signal Processing, Rome, Italy, p. 124-131, 2011 (Year: 2011).*

A. Lahreche et al., FastSEA: A Very Fast and Very Effective Matching Technique for Very Complex Time Series, 2017 International Conference on Mathematics and Information Technology, Algeria, 2017 (Year: 2017).*

Hiroaki Sakoe et al., "Dynamic Programming Algorithm Optimization for Spoken Word Recognition", IEEE Transactions on Acoustics, Speech, and Signal Processing, vol. ASSP-26, No. 1, Feb. 1978, pp. 43-49 (Total 7 pages).

J. Derek Tucker et al., "Analysis of Proteomics Data: Phase Amplitude Separation Using an Extended Fisher-Rao Metric", Electronic Journal of Statistics, vol. 8 (2014), pp. 1724-1733, ISSN: 1935-7524, DOI: 10. 1214/14-EJS900B (Total 10 pages).

* cited by examiner

MEASUREMENT DATA TABLE 128

| DEVICE ID | TIME | MEASURED VALUE |
|---|---|---|
| D1 | 2019/04/01 0:00 | 0.00 |
| D1 | 2019/04/01 0:10 | 1.70 |
| D1 | 2019/04/01 0:20 | 0.80 |
| ... | ... | ... |
| D2 | 2019/04/01 0:00 | 0.00 |
| D2 | 2019/04/01 0:10 | 0.05 |
| D2 | 2019/04/01 0:20 | 0.05 |
| ... | ... | ... |

FIG. 12

WARPING FUNCTION TABLE — 129

| BLOCK | WARPING FUNCTION | | | | | | |
|---|---|---|---|---|---|---|---|
| | 1 | 2 | 3 | 4 | 5 | 6 | ... | T |
| 1 | 1 | 3 | 3 | 4 | 5 | 5 | ... | T |
| 2 | | | | | | | ... | |
| 3 | | | | | | | ... | |
| 4 | | | | | | | ... | |
| 5 | | | | | | | ... | |

FIG. 13

DETERMINATION METHOD AND DETERMINATION APPARATUS

CROSS-REFERENCE TO RELATED APPLICATION

This application is based upon and claims the benefit of priority of the prior Japanese Patent Application No. 2019-215133, filed on Nov. 28, 2019, the entire contents of which are incorporated herein by reference.

FIELD

The embodiments discussed herein relate to a determination method and a determination apparatus.

BACKGROUND

In some situations, time-series data sets each indicating the time variation of a physical quantity such as electric energy are collected and then analyzed. For the analysis of the time-series data sets, there is correlation analysis that is to compare two time-series data sets obtained from different targets with each other to compute a correlation therebetween and evaluate the degree of similarity in terms of the time variation of the physical quantity. If the correlation is high, the existence of a causal relationship is inferred between the physical quantities measured from the different targets.

Note that, due to the timing difference between the occurrences of an event and the difference in the rate of change of the physical quantity, the two time-series data sets may have different phases and cycles and thus may have different waveforms. In this case, with simple comparison between measured values at the same location to evaluate the difference, it is not straightforward to compute a correlation with accuracy. To deal with this, as preprocessing of the correlation analysis, "alignment" may be performed to expand or compress the waveform of one of the time-series data sets in the time domain so that the waveform is similar to that of the other time-series data set. Dynamic time warping (DTW) is one of algorithms for the alignment. The alignment shifts each measured value of the one time-series data set in the time domain, thereby reducing the mismatch in phase and cycle. Using the time-series data sets after the alignment, the correlation analysis is able to evaluate the degree of similarity in the time variation of the physical quantity with accuracy.

For example, there has been proposed a respiratory sound data processing apparatus that detects adventitious sounds from respiratory sound data obtained by recording patient's respiratory sounds. The proposed respiratory sound data processing apparatus obtains a pair of respiratory sound data sets generated during different periods from the same patient and aligns one of the respiratory sound data sets with the other respiratory sound data set using the DTW. The respiratory sound data processing apparatus computes a correlation between the two respiratory sound data sets after the alignment and detects adventitious sounds on the basis of the correlation.

See, for example, Japanese Laid-open Patent Publication No. 2005-66044.

SUMMARY

According to one aspect, there is provided a non-transitory computer-readable storage medium storing a program that causes a computer to perform a process including: obtaining a first time-series data set indicating first measured values obtained by a first device during a plurality of periods including a first period and a second period and a second time-series data set indicating second measured values obtained by a second device during the plurality of periods; performing first alignment to convert positions in a time domain of first measured values belonging to the second period, based on first measured values belonging to the first period; performing second alignment to convert positions in the time domain of second measured values belonging to the second period, based on a correspondence relationship between positions before and after conversion of the first alignment; performing correlation analysis between a third time-series data set obtained by converting the first time-series data set using the first alignment and a fourth time-series data set obtained by converting the second time-series data set using the second alignment; and determining existence or absence of an inclusion relationship, based on a result of the correlation analysis, the inclusion relationship indicating that the second measured values contain a component of the first measured values.

The object and advantages of the invention will be realized and attained by means of the elements and combinations particularly pointed out in the claims.

I: is to be understood that both the foregoing general description and the following detailed description are exemplary and explanatory and are not restrictive of the invention.

BRIEF DESCRIPTION OF DRAWINGS

FIG. 12 illustrates an example of a measurement data table;

FIG. 13 illustrates an example of a warping function table;

DESCRIPTION OF EMBODIMENTS

Hereinafter, preferred embodiments will be described with reference to the accompanying drawings.

First Embodiment

A first embodiment will be described.

There may be a demand to determine, using correlation analysis, an inclusion relationship in which a component in the measured values of a time-series data set is contained in the measured values of another time-series data set. The existence of the inclusion relationship means that a physical quantity measured at one measurement location is transferred to the other measurement location. For example, the following cases are considered: a current at one measurement location flows into another measurement location; and vibration and the quantity of heat at one measurement location are transferred to another measurement location.

However, a lot of components other than the component in the measured values at the one measurement location may be contained in the measured values at the other measurement location. For example, currents other than the current at one measurement location may flow into another measurement location. Such other components become considerable noise in the correlation analysis. If direct alignment is performed between two time-series data sets containing considerable noise, the accuracy of the alignment deteriorates due to the noise. This likely leads to a decrease in the accuracy of the correlation analysis and in turn to a decrease in the accuracy of determining the inclusion relationship. In one aspect, embodiments discussed herein contributes to improve the accuracy of determining the inclusion relationship.

Figure 1:
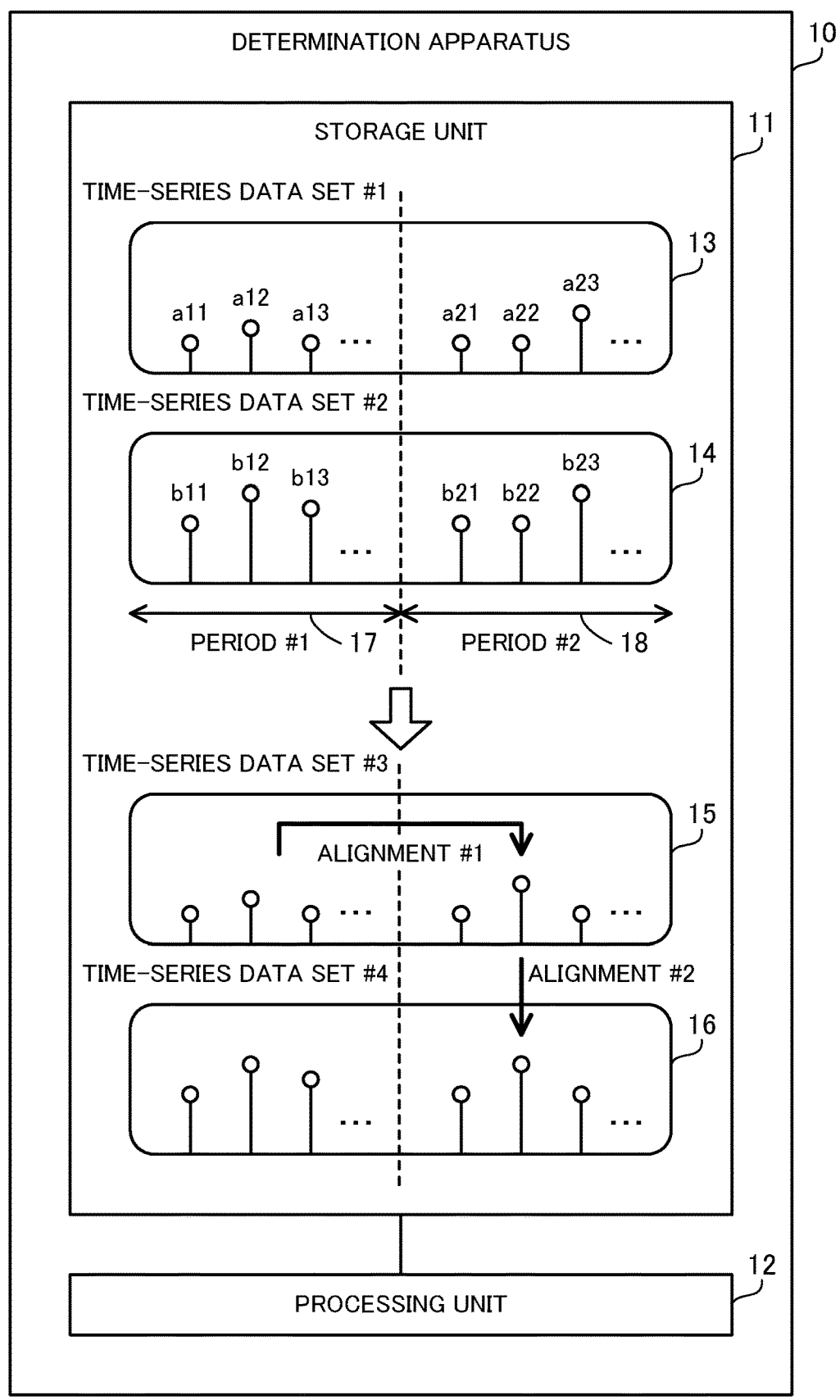
FIG. 1 is a view for explaining an example of a determination apparatus according to a first embodiment.

FIG. 1 is a view for explaining an example of a determination apparatus according to the first embodiment.

The determination apparatus 10 performs correlation analysis between two time-series data sets. The determination apparatus 10 may be a client apparatus or a server apparatus. The determination apparatus 10 may be called a computer or an information processing apparatus.

The determination apparatus 10 includes a storage unit 11 and a processing unit 12. The storage unit 11 may be a volatile semiconductor memory such as a random access memory (RAM), or a non-volatile storage device such as a hard disk drive (HDD) or a flash memory. The processing unit 12 is a processor such as a central processing unit (CPU), a graphics processing unit (GPU), or a digital signal processor (DSP), for example. In this connection, the processing unit 12 may include an application-specific electronic circuit such as an application-specific integrated circuit (ASIC) or a field programmable gate array (FPGA). The processor executes programs stored in a memory such as a RAM (may be the storage unit 11). A set of multiple processors may be a "multiprocessor" or simply a "processor."

The storage unit 11 stores therein time-series data sets 13 and 14. The time-series data set 13 indicates a series of measured values obtained by a device during a plurality of periods including periods 17 and 18. The time-series data set 14 indicates a series of measured values obtained by a device different from that used for the time-series data set 13, during the same periods as those for the time-series data set 13. The time-series data sets 13 and 14 may be called signal sequences.

The periods 17 and 18 have a prescribed duration, like 24 hours. A measured value is obtained at intervals, like 10-minute intervals, which are sufficiently shorter than the duration of the periods 17 and 18. The measured values in the time-series data set 13 and the measured values in the time-series data set 14 are obtained by devices at different locations. The devices are sensor devices for measuring a physical quantity. For example, the devices are ammeters for measuring current, vibrometers for measuring the amount of vibration, thermometers for measuring temperature, or others. The time-series data sets 13 and 14 have almost periodicity, in which a waveform indicating the time variation of measured values is similar across a plurality of periods. Therefore, in the time-series data set 13, the waveform in the period 17 and the waveform in the period 18 are similar. In addition, in the time-series data set 14, the waveform in the period 17 and the waveform in the period 18 are similar.

The time-series data set 13 includes measured values $a11$, $a12$, $a13$, . . . belonging to the period 17 and measured values $a21$, $a22$, $a23$, . . . belonging to the period 18. The time-series data set 14 includes measured values $b11$, $b12$, $b13$, . . . belonging to the period 17 and measured values $b21$, $b22$, $b23$, . . . belonging to the period 18.

The processing unit 12 performs alignment on the measured values belonging to the period 18 of the time-series data set 13 on the basis of the time variation of the measured values belonging to the period 17 of the time-series data set 13. For this alignment, an algorithm such as dynamic time warping (DTW) is used. This alignment converts the positions in the time domain of the measured values belonging to the period 18 of the time-series data set 13 so that the waveform in the period 18 has a high degree of similarity to that in the period 17 of the time-series data set 13.

I: may be said that the alignment converts the time points of the measured values or expands or compresses the waveform in the time direction. In this connection, the positions are converted within the same period without changing the order of the plurality of measured values. With the alignment, the correspondence relationship between the positions before and after the conversion is detected for the period 18. A function of computing a position after conversion from a position before conversion may be called a warping function.

The processing unit 12 applies, to the time-series data set 14, the correspondence relationship obtained by performing the alignment on the time-series data set 13. More specifically, the processing unit 12 performs the alignment on the measured values belonging to the period 18 of the time-series data set 14 on the basis of the above correspondence relationship obtained for the period 18. This alignment converts the positions in the time domain of the measured values belonging to the period 18 of the time-series data set 14.

In this connection, the alignment is performed, in two stages, for the periods other than the periods 17 and 18 in the same manner as described above. First, the alignment in the first stage is performed on the measured values belonging to another period of the time-series data set 13, to match the waveform in the period 17 of the time-series data set 13. Then, the alignment in the second stage is performed on the measured values belonging to the other period of the time-series data set 14 on the basis of the correspondence relationship obtained for the other period. This alignment may be called as indirect alignment, since the time-series data sets 13 and 14 are not directly compared with each other.

The alignment in the first stage converts the time-series data set 13 into a time-series data set 15. The alignment in the second stage converts the time-series data set 14 into a time-series data set 16. The processing unit 12 performs correlation analysis between the time-series data set 15 and the time-series data set 16. For example, the processing unit 12 computes an index value such as a correlation coefficient in the time domain. Alternatively, for example, the processing unit 12 transforms each time-series data set 15 and 16 into a frequency spectrum and computes an index value such as a correlation coefficient in the frequency domain.

The processing unit 12 determines the existence or absence of an inclusion relationship in which the time-series data set 13 is included in the time-series data set 14, on the basis of the result of the correlation analysis. The inclusion relationship here means that a component (for example, the measured values themselves of the time-series data set 13 or their attenuated values) in the measured values of the time-series data set 13 is contained in the measured values of the time-series data set 14. Note that other components are contained in the measured values of the time-series data set 14.

Each measured value of the time-series data set 14 may be a combination of physical quantities caused due to different factors. In this connection, at the measurement location for the time-series data set 14, a physical quantity from the measurement location for the time-series data set 13 and other physical quantities may be combined. For example, a current from the measurement location for the time-series data set 13 and another current flow to the measurement location for the time-series data set 14. As another example, vibration and the quantity of heat at the measurement location for the time-series data set 13 and vibration and the quantity of heat at another location are transferred to the measurement location for the time-series data set 14. In these cases, the time-series data sets 13 and 14 have the inclusion relationship. On the other hand, in the case where any physical quantity from the measurement location for the time-series data set 13 is not combined at the measurement location for the time-series data set 14, the time-series data sets 13 and 14 do not have the inclusion relationship.

As the time-series data sets 13 and 14 have a higher correlation, they more likely have the inclusion relationship, and vice versa. For example, the processing unit 12 infers the existence of the inclusion relationship when a correlation coefficient is greater than a threshold.

As described above, the determination apparatus 10 of the first embodiment performs correlation analysis between the time-series data sets 13 and 14 and determines the existence or absence of an inclusion relationship in which a component in the time-series data set 13 is included in the time-series data set 14, on the basis of the result of the correlation analysis. This provides information useful for various measures such as maintenance of wiring running through measurement locations. In addition, as preprocessing of the correlation analysis, the alignment of expanding or compressing each time-series data set 13 and 14 in the time direction is performed. This contributes to detection of a higher correlation if they have the inclusion relationship, thereby improving the accuracy of determining the inclusion relationship.

In addition, using the almost periodicity of the time-series data sets 13 and 14, indirect alignment is performed in such a way that alignment is performed between the measured values in different periods of the time-series data set 13 and then this alignment method is applied to the measured values of the time-series data set 14. This achieves the alignment with high accuracy when the time-series data sets 13 and 14 have the inclusion relationship, even if the time-series data set 14 has much noise, as compared with direct alignment of comparing the time-series data sets 13 and 14 with each other. As a result, in the case where the inclusion relationship exists, a higher correlation is detected. That is, this approach improves the accuracy of determining the inclusion relationship.

In this connection, components other than a component of the time-series data set 13 among the components contained in the time-series data set 14 are regarded as noise in the correlation analysis between the time-series data sets 13 and 14. Especially, if the component of the time-series data set 13 and the other components are not synchronized, the other components are regarded as considerable noise. For this reason, there is a possibility that a high correlation is not detected due to the noise, even if the inclusion relationship exists. Thus, the accuracy of determining the inclusion relationship is likely decreased. By contrast, the above-described indirect alignment makes it possible to detect a high correlation while mitigating the effect of noise in the case where the inclusion relationship exists.

Second Embodiment

A second embodiment will now be described.

Figure 2:
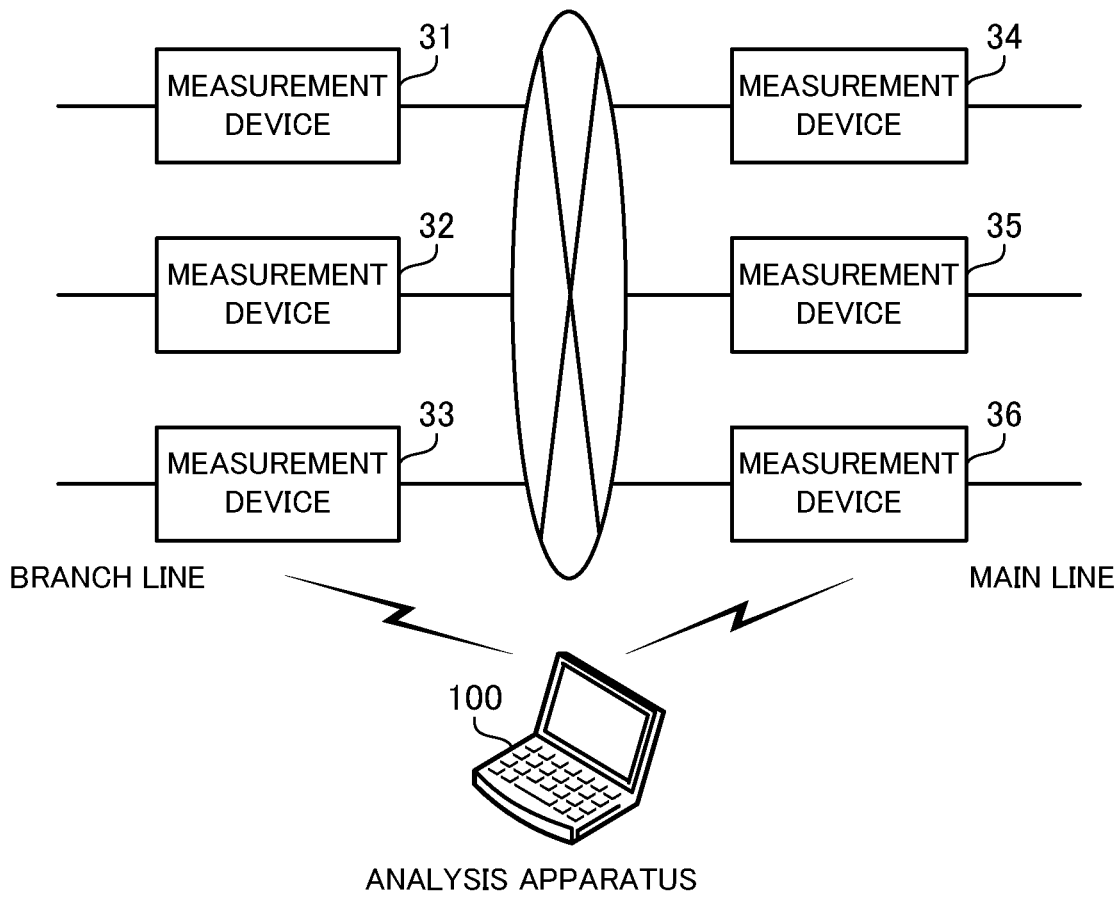
FIG. 2 illustrates an example of an information processing system according to a second embodiment.

FIG. 2 illustrates an example of an information processing system according to the second embodiment.

The information processing system of the second embodiment performs correlation analysis between two signal sequences measured at different locations and determines the existence or absence of "inclusion relationship." The "inclusion relationship" indicates that one signal sequence has a waveform that contains the other signal sequence. The information processing system of the second embodiment includes measurement devices 31, 32, 33, 34, 35, and 36 and an analysis apparatus 100.

The measurement devices 31, 32, 33, 34, 35, and 36 are sensor devices each of which continuously measures the same type of physical quantity. These measurement devices 31, 32, 33, 34, 35, and 36 are installed at different locations. The physical quantity to be measured expresses the magnitude of a physical phenomenon such as current, voltage, or vibration and is represented by a signal level at a certain time point.

The measurement devices 31, 32, and 33 measure the physical quantities on mutually different "branch lines," whereas the measurement devices 34, 35, and 36 measure the physical quantities on mutually different "main lines." The physical quantities on two or more branch lines are combined on a main line. Therefore, a measured value obtained by the measurement device 34 is likely a combination of a part or all of the measured values obtained by the measurement devices 31, 32, and 33. Similarly, a measured value obtained by the measurement device 35 is likely a combination of a part or all of the measured values obtained by the measurement devices 31, 32, and 33. A measured value obtained by the measurement device 36 is likely a combination of a part or all of the measured values obtained by the measurement devices 31, 32, and 33. Note that the measured values of the measurement devices 34, 35, and 36 may include noise.

A situation in which a certain branch line joins a main line and a physical quantity on the branch line is contained in a physical quantity on the main line may be called "inclusion relationship." In the second embodiment, the inclusion relationship between measured values obtained by the measurement devices 31, 32, and 33 on the branch lines and measured values obtained by the measurement devices 34, 35, and 36 on the main lines is uncertain. For example, there is a possibility that the branch line where the measurement device 31 is located does or does not join the main line where the measurement device 34 is located.

The measurement devices 31, 32, 33, 34, 35, and 36 may be ammeters for measuring current flowing through wires. In this case, the inclusion relationship may represent a connection relationship in which a certain branch line connects to a main line and the current in the branch line flows into the main line. In addition, the inclusion relationship may represent crosstalk (crossed line) in which a signal on a branch line propagates to a main line even if the branch line does not connect to the main line. Alternatively, the measurement devices 31, 32, 33, 34, 35, and 36 may be vibrometers for measuring the vibration of a machine. In this case, the inclusion relationship may represent a propagation relationship in which vibration at a certain location propagates to another location. In the case of vibration, the "main lines" correspond to locations where vibration of a plurality of machines is concentrated. As described above, the second embodiment is applicable to various physical quantities and inclusion relationships.

The analysis apparatus 100 performs correlation analysis between a signal sequence indicating the time variation of measured values on a branch line and a signal sequence indicating the time variation of measured values on a main line, and determines the existence or absence of the inclusion relationship. The analysis apparatus 100 continuously collects measured values obtained by the measurement devices 31, 32, 33, 34, 35, and 36. The analysis apparatus 100 may receive the measured values from the measurement devices 31, 32, 33, 34, 35, and 36 through wireless or wired communication, may read the measured values from a storage medium on which the measured values are recorded, or may receive inputs of the measured values from a user. As an example, the second embodiment describes a case of determining the inclusion relationship between the measured values obtained by the measurement device 31 and the measured values obtained by the measurement device 34. A signal indicating the measured values obtained by the measurement device 34 on the main line may be referred to as a "target signal," whereas the measured values obtained by the measurement device 31 on the branch line may be referred to as a "reference signal."

Figure 3:
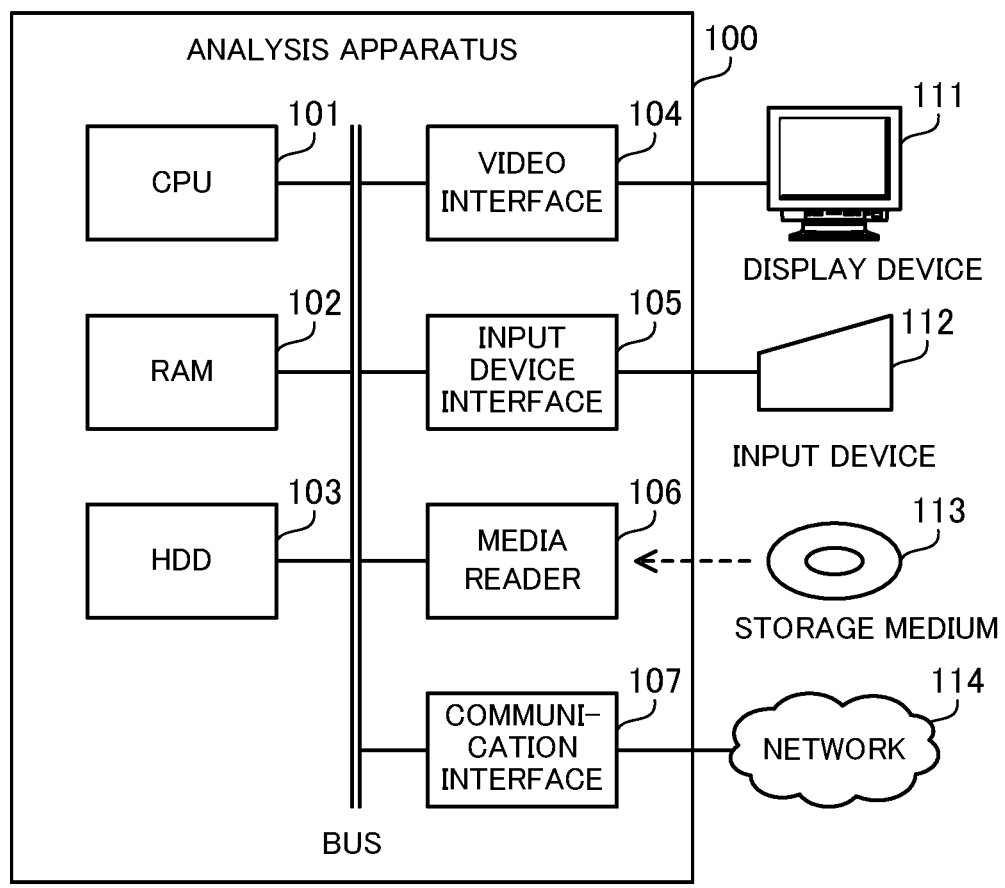
FIG. 3 is a block diagram illustrating an example of a hardware configuration of an analysis apparatus.

FIG. 3 is a block diagram illustrating an example of a hardware configuration of an analysis apparatus.

The CPU 101 is a processor that executes program instructions. The CPU 101 loads at least part of a program and data from the HDD 103 to the RAM 102 and executes the program. The CPU 101 may include a plurality of processor cores, and the analysis apparatus 100 may include a plurality of processors. A set of multiple processors may be called a "multiprocessor" or simply a "processor."

The RAM 102 is a volatile semiconductor memory that temporarily stores a program to be run by the CPU 101 and data to be used by the CPU 101 in processing. In this connection, the analysis apparatus 100 may include another type of memory than RAM or may include a plurality of memories.

The HDD 103 is a non-volatile storage device that stores software programs such as operating system (OS), middleware and application software, and data. In this connection, the analysis apparatus 100 may include another type of storage device, such as a flash memory or a solid state drive (SSD), or may include a plurality of storage devices.

The video interface 104 outputs videos to a display device 111 connected to the analysis apparatus 100 in accordance with instructions from the CPU 101. The display device 111 may be any type of display device such as a cathode ray tube (CRT) display, a liquid crystal display (LCD), organic electro-luminescence (OEL) display, or a projector. Another output device than the display device 111, such as a printer, may be connected to the analysis apparatus 100.

The input device interface 105 receives an input signal from an input device 112 connected to the analysis apparatus 100. As the input device 112, any type of input device such as a mouse, a touch panel, a touch pad, or a keyboard may be used. In addition, plural types of input devices may be connected to the analysis apparatus 100.

The media reader 106 is a reading device that reads programs and data from a storage medium 113. As the storage medium 113, any type of storage medium may be used, such as a magnetic disk, an optical disc, or a semiconductor memory. Examples of the magnetic disk include a flexible disk (FD) and an HDD, and examples of the optical disc include a compact disc (CD) and a digital versatile disc (DVD). For example, the media reader 106 copies a program or data read from the storage medium 113 to another storage medium such as the RAM 102 or HDD 103. The read program is executed by the CPU 101, for example. In this connection, the storage medium 113 may be a portable storage medium and be used for distribution of the program and data. In addition, the storage medium 113 and HDD 103 may be called computer-readable storage media.

The communication interface 107 is connected to a network 114 and communicates with the measurement devices 31, 32, 33, 34, 35, and 36 and other information processing apparatuses over the network 114. The communication interface 107 may be a wired communication interface that is connected to a wired communication device, such as a switch or a router, or may be a wireless communication interface that is connected to a wireless communication device, such as a base station or an access point.

The following describes correlation analysis between a target signal and a reference signal.

Figure 4:
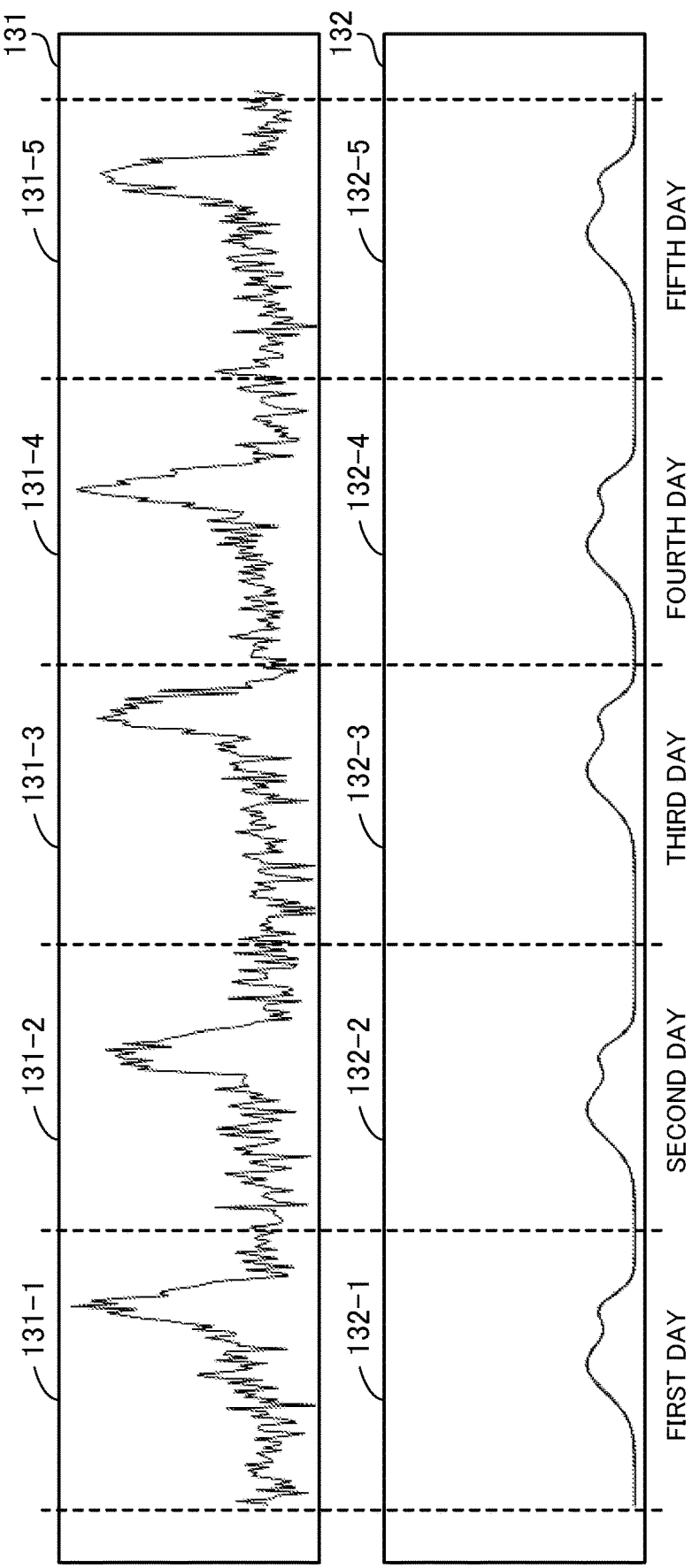
FIG. 4 illustrates an example of a target signal and a reference signal.

FIG. 4 illustrates an example of a target signal and a reference signal.

The analysis apparatus 100 obtains a signal sequence 131 indicating the time variation of measured values obtained by the measurement device 34 on a main line and a signal sequence 132 indicating the time variation of measured values obtained by the measurement device 31 on a branch line. The signal levels of the signal sequences 131 and 132 indicate currents, for example. The signal in the signal sequence 131 is a target signal and the signal in the signal sequence 132 is a reference signal.

The signal sequences 131 and 132 are "almost-periodic signal" having almost periodicity. An almost-periodic signal is a signal sequence that does not have perfect periodicity but has similar waveforms repeated at prescribed intervals T. A signal sequence f with almost periodicity satisfies an expression (1). In the expression (1), "t" is a certain time point and "ε" is an acceptable error. That is, the absolute value of the difference between a signal f(t) at time t and a signal f(t+T) at time t+T, which is time T thereafter, is less than or equal to the acceptable error ε. In the case of ε=0, the signal sequence f is a perfectly periodic signal with intervals of T.

$$|f(t+T) - f(t)| \leq \varepsilon \qquad (1)$$

The signal sequences 131 and 132 are, for example, time-series data sets that each have a 24-hour cycle and include measured values of current obtained at 10-minute intervals. For example, the signal sequences 131 and 132 each represent the time variation of power consumption. Power is rarely consumed exactly in the same way at the same time on different days due to various factors such as accidental events and unusual events. However, human daily rhythm is almost constant. Therefore, there exists a common tendency as a whole in the time variation of power consumption among different days. Therefore, a signal sequence indicating the time variation of power consumption may be taken as an almost-periodic signal with a 24-hour cycle.

The signal sequences 131 and 132 are each divided into a plurality of blocks with a duration of 24 hours. The signal sequence 131-1 represents the first day in the signal sequence 131. The signal sequence 131-2 represents the second day in the signal sequence 131. The signal sequence 131-3 represents the third day in the signal sequence 131. The signal sequence 131-4 represents the fourth day in the signal sequence 131. The signal sequence 131-5 represents the fifth day in the signal sequence 131. The signal sequence 132-1 represents the first day in the signal sequence 132. The signal sequence 132-2 represents the second day in the signal sequence 132. The signal sequence 132-3 represents the third day in the signal sequence 132. The signal sequence 132-4 represents the fourth day in the signal sequence 132. The signal sequence 132-5 represents the fifth day in the signal sequence 132.

The analysis apparatus 100 performs correlation analysis between the signal sequence 131 and the signal sequence 132. If a high correlation is detected, it is inferred that the following inclusion relationship exists: the signal sequence 132 is one of two or more signal sequences on branch lines combined into the signal sequence 131. If a low correlation is detected, it is inferred that such an inclusion relationship does not exist.

As a correlation index, the following are considered: a correlation coefficient computed in the time domain, a correlation coefficient computed in the frequency domain, and a phase correlation index (coherence) computed in the frequency domain.

The correlation coefficient $\rho_T$ in the time domain is computed using an expression (2). In the expression (2), f is a signal sequence serving as a reference signal, and g is a signal sequence serving as a target signal. In this connection, the signal sequences f and g are centralized so that the average signal level becomes zero. $\sigma_{fg}$ is the covariance of the signal sequences f and g, $\sigma_g$ is the standard deviation of the signal sequence f, and $\sigma_g$ is the standard deviation of the signal sequence g. T is the number of samples in each signal sequence f and g in the time domain.

$$\rho_T = \frac{\sigma_{fg}}{\sigma_f \sigma_g} = \frac{\frac{1}{T}\sum_{t=1}^{T} f(t)g(t)}{\sqrt{\frac{1}{T}\sum_{t=1}^{T} f(t)^2}\sqrt{\frac{1}{T}\sum_{t=1}^{T} g(t)^2}} \quad (2)$$

The correlation coefficient $\rho_r$ in the frequency domain is computed using an expression (3). In the expression (3), F is a frequency spectrum obtained by transforming the signal sequence f using a discrete Fourier transform, and G is a frequency spectrum obtained by transforming the signal sequence g using the discrete Fourier transform. N is the number of angular frequency samples, and $\omega_k$ is the k-th angular frequency. Re [ ] is a function of computing the real part of a complex number. F* ($\omega$) is a conjugate complex number of a frequency component F($\omega$). $K_{fg}$ is the cospectrum of the signal sequences f and g, $S_{fg}$ is the cross-spectrum of the signal sequences f and g. $C_{ff}$ is the autocorrelation function of the signal sequence f corresponding to the frequency spectrum F, and $C_{gg}$ is the autocorrelation function of the signal sequence g corresponding to the frequency spectrum G. $C_{ff}(\tau)$ is an average of values obtained by multiplying a signal f(t) by a signal f(t+$\tau$) that is separate by $\tau$ from the signal f(t) in the signal sequence f. $C_{gg}(t)$ is an average of values obtained by multiplying a signal g(t) by a signal g(t+$\tau$) that is separate by $\tau$ from the signal g(t) in the signal sequence g. According to Parseval's identity, it is known that $C_{ff}(0)$ is equal to the mean square value of the amplitude in the frequency spectrum P of the full band, and $C_{gg}(0)$ is equal to the mean square value of the amplitude in the frequency spectrum G of the full band.

$$\rho_F = \frac{1}{\sqrt{C_{ff}(0)}\sqrt{C_{gg}(0)}} \int_{-\infty}^{\infty} K_{fg}(\omega)d\omega \quad (3)$$

$$= \frac{1}{\sqrt{C_{ff}(0)}\sqrt{C_{gg}(0)}} \int_{-\infty}^{\infty} \text{Re}[S_{fg}(\omega)]d\omega$$

$$= \frac{\sum_{k=1}^{N} \text{Re}[F*(\omega_k)G(\omega_k)]}{\sqrt{\sum_{k=1}^{N} |F(\omega_k)|^2}\sqrt{\sum_{k=1}^{N} |G(\omega_k)|^2}}$$

The coherence $\text{Coh}_{fg}$ in the frequency domain is computed using an expression (4). The overall coherence $\text{Coh}_{fg}$ is the total coherence $\text{coh}_{fg}$ across angular frequencies. The coherence $\text{coh}_{fg}$ at each angular frequency is computed using an expression (5). In the expression (5), M is the number of blocks into which each signal sequence f and g is divided. $F_i$ is a frequency spectrum obtained by transforming the signal sequence f in the i-th block using the discrete Fourier transform. $G_i$ is a frequency spectrum obtained by transforming the signal sequence g in the i-th block using the discrete Fourier transform. $\theta_i(\omega)$ is the phase of a frequency component with the angular frequency $\omega$ contained in the frequency spectrum $F_i$. $\eta_i(\omega)$ is the phase of a frequency component with the angular frequency $\omega$ contained in the frequency spectrum $G_1$.

$$\text{Coh}_{fg} = \sum_{k=1}^{N} \text{coh}_{fg}(\omega_k) \quad (4)$$

$$\text{coh}_{fg}(\omega_k) = \frac{\sum_{i=1}^{M} |F_i(\omega_k)||G_i(\omega_k)|\cos(\theta_i(\omega_k) - \eta_i(\omega_k))}{\sqrt{\sum_{i=1}^{M} |F_i(\omega_k)|^2}\sqrt{\sum_{i=1}^{M} |G_i(\omega_k)|^2}} \quad (5)$$

The coherence $\text{coh}_{fg}$ at each angular frequency corresponds to the real part of a complex number called the complex degree of spatial coherence. Assume now that an amplitude mismatch is sufficiently small, as compared with a phase mismatch, across a plurality of blocks. Therefore, assume that, throughout all blocks i=1 to M, the absolute values of frequency component $F_i(\omega)$ are the same and the absolute values of frequency component $G_i(\omega)$ are the same. In this case, the coherence $coh_{fg}$ at each angular frequency is approximated by an expression (6). It is understood from the approximate expression (6) that the coherence $coh_{fg}$ is a phase-oriented index.

$$coh_{fg}(\omega_k) \sim \frac{|F(\omega_k)||G(\omega_k)|\sum_{i=1}^{M}\cos(\theta_i(\omega_k) - \eta_i(\omega_k))}{\sqrt{M|F(\omega_k)|^2}\sqrt{M|G(\omega_k)|^2}} \qquad (6)$$

$$= \frac{1}{M}\sum_{i=1}^{M}\cos(\theta_i(\omega_k) - \eta_i(\omega_k))$$

As described above, the analysis apparatus 100 computes a correlation index such as a correlation coefficient or a coherence between the signal sequences 131 and 132. However, since the signal sequence 131 on a main line is a combination of signal sequences on a plurality of branch lines, the signal sequence 131 has a lot of noise in view of the signal sequence 132 on a branch line. For this reason, the use of the signal sequences 131 and 132 as they are to compute a correlation index such as a correlation coefficient or a coherence therebetween deteriorates the accuracy of the correlation analysis. To deal with this, as preprocessing of the correlation analysis, the analysis apparatus 100 performs alignment that is to expand or compress at least one of the signal sequences 131 and 132 in the time domain so that the waveforms of the signal sequences 131 and 132 are as similar to each other as possible.

One of considered alignment methods is to perform direct alignment in which, with one of a signal sequence of one block in the signal sequence 131 and a signal sequence of the corresponding block in the signal sequence 132 as a base, the other signal sequence is expanded or compressed in the time domain. However, since the signal sequence 131 has a lot of noise, the signal sequence 131 and the signal sequence 132 may have greatly different waveforms. Thus, this direct alignment may deteriorate the accuracy of the alignment itself. By contrast, using the features that the signal sequences 131 and 132 are almost-periodic signals and each have similarity across blocks, the analysis apparatus 100 performs indirect alignment, described below.

Figure 5:
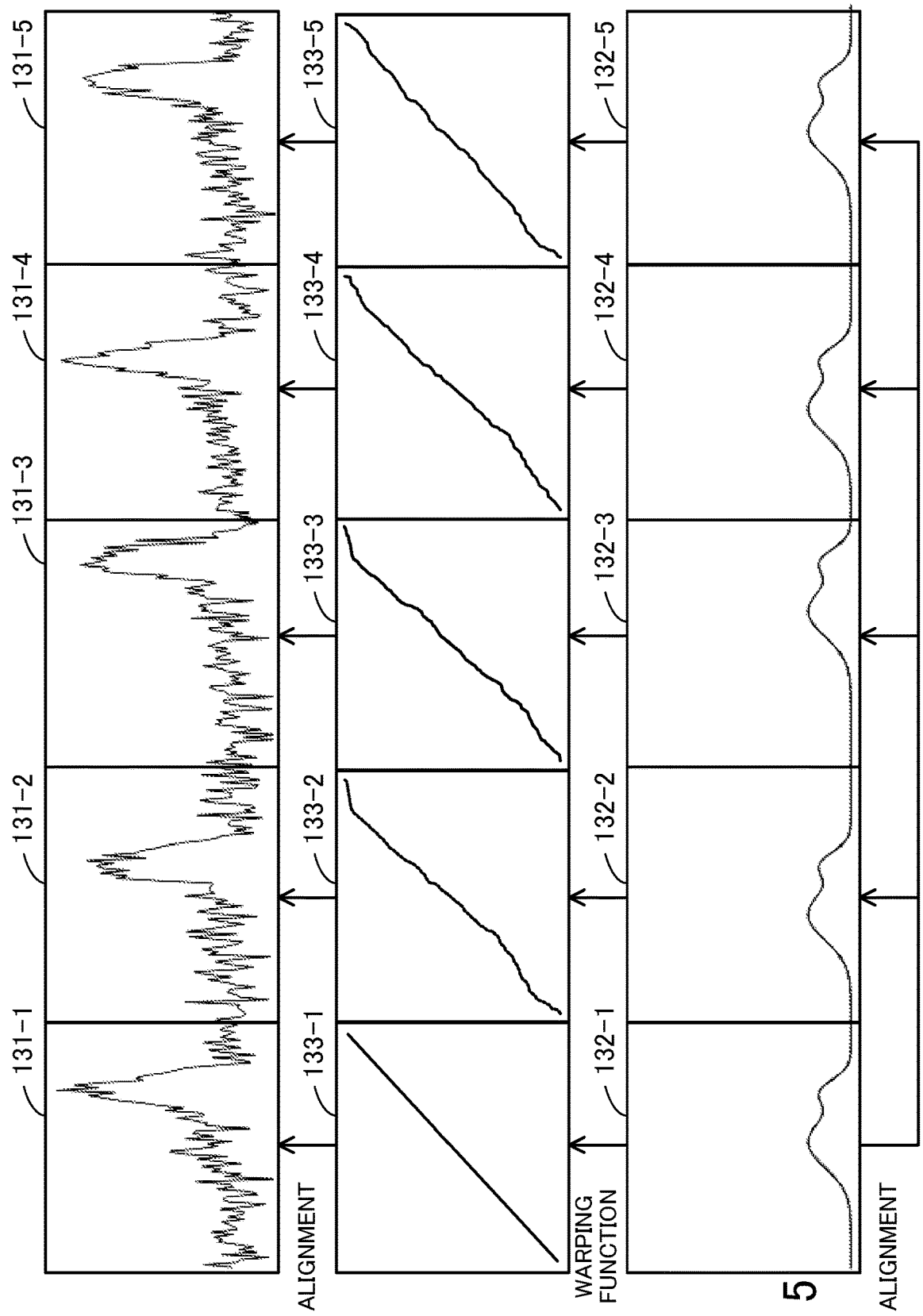
FIG. 5 illustrates an example of alignment between a target signal and a reference signal.

FIG. 5 illustrates an example of alignment between a target signal and a reference signal.

The analysis apparatus 100 selects one of a plurality of blocks as a base block. The base block may be a fixed block or may be randomly selected. For example, the beginning block (first day) among the plurality of blocks is selected as the base block.

The analysis apparatus 100 selects a signal sequence 132-1 belonging to the base block from the signal sequence 132 on a branch line. The analysis apparatus 100 performs alignment to expand or compress each signal sequence 132-2 to 132-5 belonging to the other blocks of the signal sequence 132 in the time direction, using the signal sequence 132-1 as the base signal. Here, the signal sequence 132-2 is expanded or compressed to become similar to the signal sequence 132-1. The signal sequence 132-3 is expanded or compressed to become similar to the signal sequence 132-1. The signal sequence 132-4 is expanded or compressed to become similar to the signal sequence 132-1. The signal sequence 132-5 is expanded or compressed to become similar to the signal sequence 132-1.

With the alignment of the signal sequence 132, warping functions 133-1 to 133-5 are generated. The warping functions 133-1 to 133-5 are each a function of computing a position (time point) of the signal after alignment from a position (time point) of the signal before alignment.

The warping function 133-1 corresponds to the signal sequence 132-1 and is an identity function that returns the same output as given in the input. This is because the alignment is not performed on the signal sequence 132-1. The warping function 133-2 corresponds to the signal sequence 132-2 and is generated through the alignment of the signal sequence 132-2. The warping function 133-3 corresponds to the signal sequence 132-3 and is generated through the alignment of the signal sequence 132-3. The warping function 133-4 corresponds to the signal sequence 132-4 and is generated through the alignment of the signal sequence 132-4. The warping function 133-5 corresponds to the signal sequence 132-5 and is generated through the alignment of the signal sequence 132-5.

The analysis apparatus 100 performs alignment that is to expand or compress each signal sequence 131-1 to 131-5 included in the signal sequence 131 on a main line in the time direction using the corresponding warping function. Here, the signal sequence 131-1 is expanded or compressed using the warping function 133-1. Note that, since the warping function 133-1 is an identity function, the signal sequence 131-1 is not substantially subjected to the alignment. The signal sequence 131-2 is expanded or compressed using the warping function 133-2. The signal sequence 131-3 is expanded or compressed using the warping function 133-3. The signal sequence 131-4 is expanded or compressed using the warping function 133-4. The signal sequence 131-5 is expanded or compressed using the warping function 133-5.

That is to say, the alignment is performed on the signal sequences 131-1 and 132-1 in the first block with the same warping function 133-1. The alignment is performed on the signal sequences 131-2 and 132-2 in the second block with the same warping function 133-2. The alignment is performed on the signal sequences 131-3 and 132-3 in the third block with the same warping function 133-3. The alignment is performed on the signal sequences 131-4 and 132-4 in the fourth block with the same warping function 133-4. The alignment is performed on the signal sequences 131-5 and 132-5 in the fifth block with the same warping function 133-5. Note that these warping functions 133-1 to 133-5 are not determined by comparing the signal sequences 131 and 132 with each other but are determined using the signal sequence 132 on the branch line.

Examples of an algorithm for the alignment include dynamic time warping (DTW) and elastic shape analysis (ESA). For the DTW, please see, for example, the following document: Hiroaki Sakoe and Seibi Chiba, "Dynamic Programming Algorithm Optimization for Spoken Word Recognition," IEEE Transaction on Acoustics, Speech and Signal Processing, Vol. ASSP-26, No. 1, pp. 43-49, February 1978. For the ESA, please see, for example, the following document: Derek Tucker, Wei Wu and Anuj Srivastava, "Analysis of proteomics data: Phase amplitude separation using an extended Fisher-Rao metric," Electronic Journal of Statistics, Vol. 8, No. 2, pp. 1724-1733, 2014. The following describes an example of the DTW algorithm.

Figure 6:
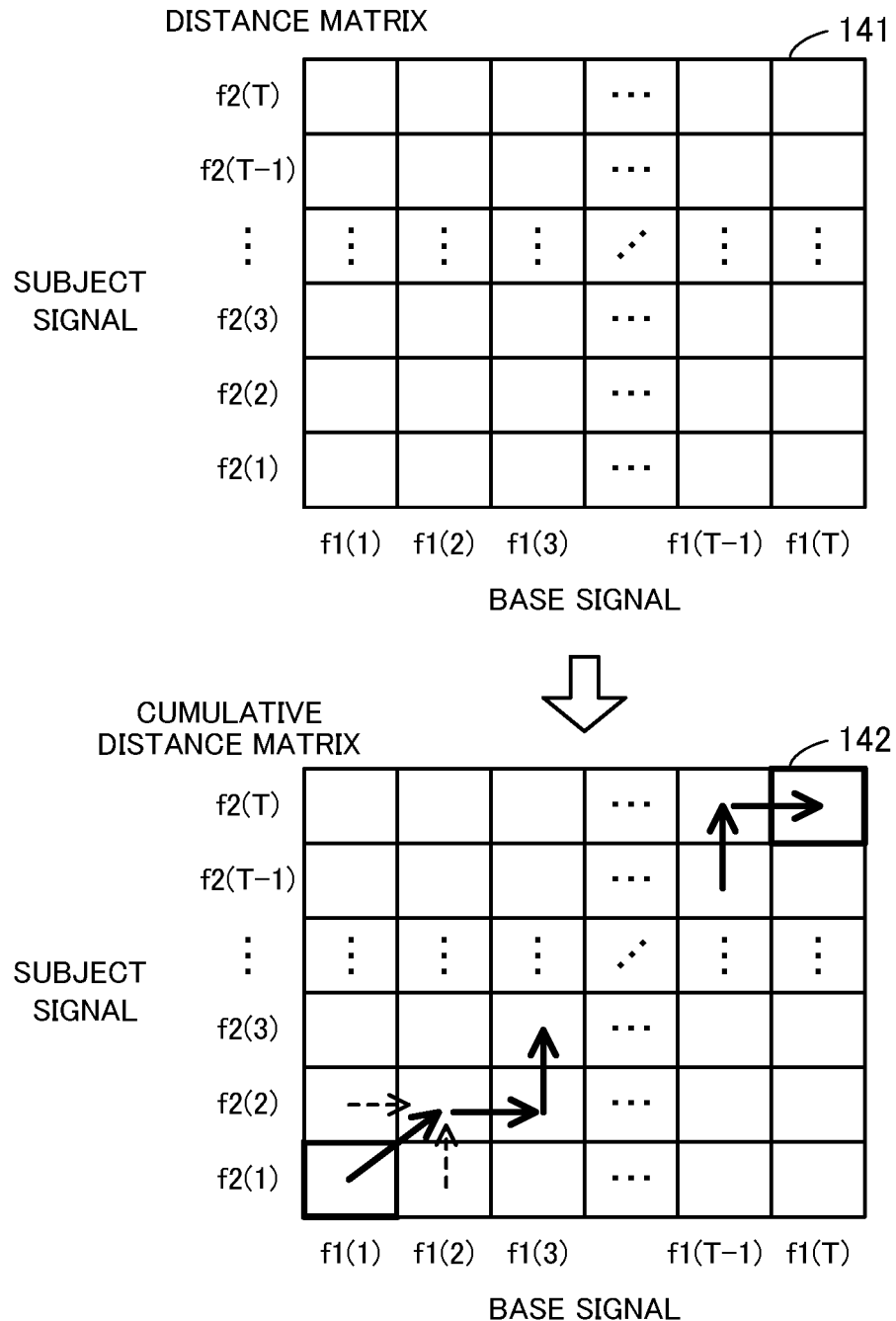
FIG. 6 illustrates an example of alignment.

FIG. 6 illustrates an example of alignment.

The following describes a case where the positions of subject signals f2(1), f2(2), f2(3), . . . , f2(T−1), and f2(T) are adjusted to be as similar as possible to those of base signals f1(1), f1(2), f1(3), . . . , f1(T−1), and f1(T). The analysis apparatus 100 generates a T-by-T distance matrix 141 and a T-by-T cumulative distance matrix 142.

An element (x, y) of the distance matrix 141 represents the distance between the subject signal f2(x) and the base signal f1(y). The distance is, for example, the absolute value or square of the difference between signal levels. As the subject signal f2(x) and the base signal f1(y) are closer, the element (x, y) of the distance matrix 141 represents a smaller distance. The analysis apparatus 100 computes the distance with respect to all combinations of the T base signals and the T subject signals in the distance matrix 141.

The element (1, 1) of the cumulative distance matrix 142 is the same as the element (1, 1) of the distance matrix 141. Assuming that x is an integer of two or greater, the element (x, 1) of the cumulative distance matrix 142 is a value obtained by adding the element (x, 1) of the distance matrix 141 to the element (x−1, 1) of the cumulative distance matrix 142. Assuming that y is an integer of two or greater, the element (1, y) of the cumulative distance matrix 142 is a value obtained by adding the element (1, y) of the distance matrix 141 to the element (1, y−1) of the cumulative distance matrix 142. Assuming that x and y are both integers of two or greater, the element (x, y) of the cumulative distance matrix 142 is a value obtained by adding the element (x, y) of the distance matrix 141 to the minimum value among the elements (x−1, y−1), (x, y−1), and (x−1, y) of the cumulative distance matrix 142. In this manner, the cumulative distances are sequentially computed from the element (1, 1) toward the element (T, T).

The cumulative distance at the element (T, T) of the cumulative distance matrix 142 corresponds to a degree of similarity between the base signal and the subject signal after alignment. In addition, the path from the element (1, 1) to the element (T, T) indicates a correspondence relationship that provides the highest degree of similarity between the base signal and the subject signal, and corresponds to a warping function. The element (x, y) on the path in the cumulative distance matrix 142 indicates that the subject signal f2(x) is shifted to the position y through alignment.

In this connection, a warping function may map two or more different positions (time points) before alignment to the same position (time point) after alignment. This corresponds to a compression in the time domain. In this case, the analysis apparatus 100 may average the two or more original signals at the former positions and take the average value as the converted signal at the latter position. In addition, a warping function may map one position (time position) before alignment to two or more consecutive positions (time positions) after alignment. This corresponds to an expansion in the time domain. In this case, the analysis apparatus 100 may copy the original signal at the former position and take the copied signals as the converted signals at the latter positions. In addition, the analysis apparatus 100 may perform linear interpolation for intermediate signals on the basis of two or more consecutive signals, adjacent to each other, for smooth change.

The following describes correlation analysis that is performed after alignment is performed as preprocessing. The following describes four methods as examples of the correlation analysis.

Figure 7:
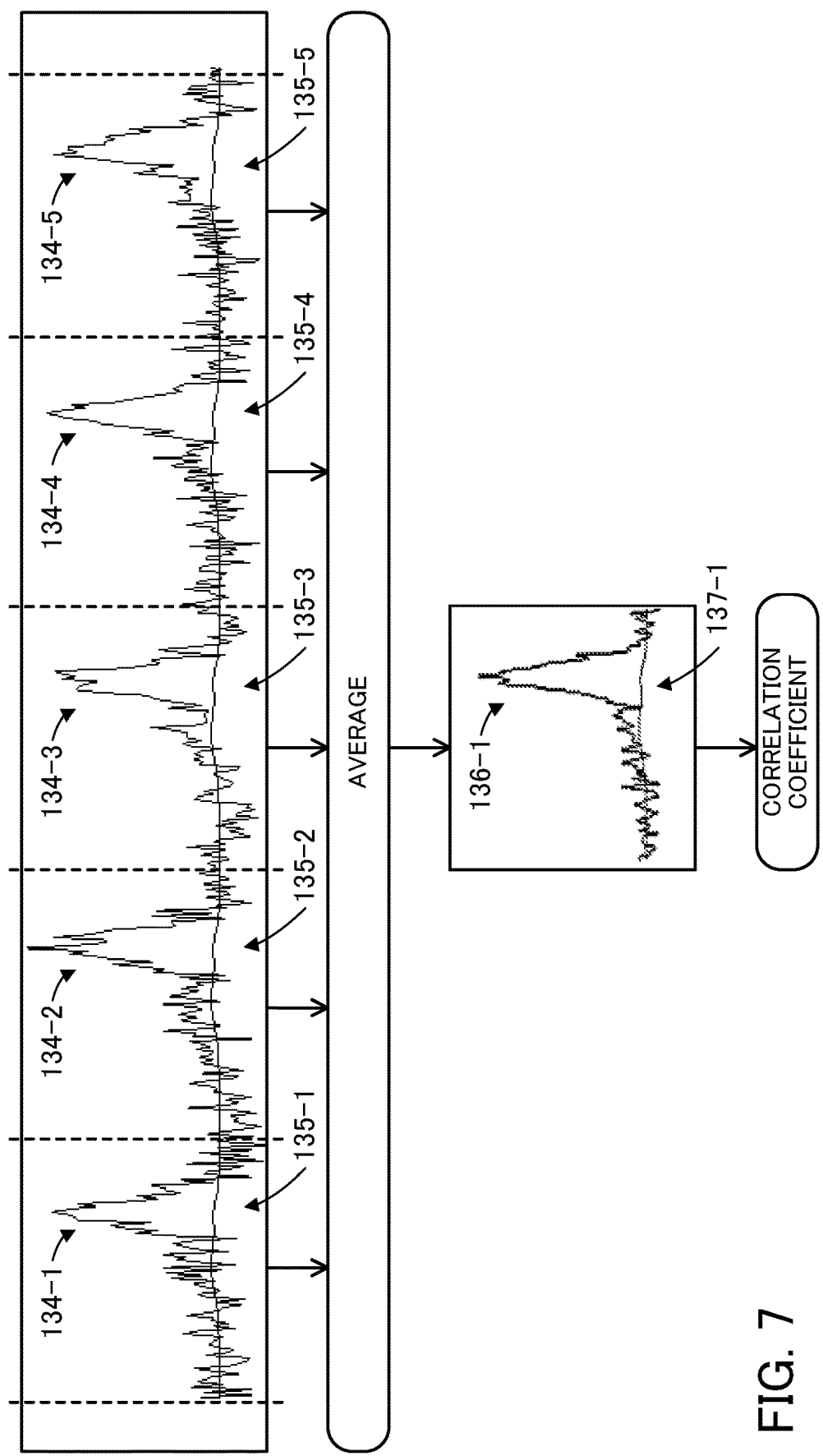
FIG. 7 illustrates a first example of correlation analysis.

FIG. 7 illustrates a first example of correlation analysis.

Through the above-described alignment, signal sequences 134-1 to 134-5 and signal sequences 135-1 to 135-5 are generated. The signal sequences 134-1 to 134-5 are of a target signal, whereas the signal sequences 135-1 to 135-5 are of a reference signal.

The signal sequence 134-1 is the same as the signal sequence 131-1. The signal sequence 134-2 is obtained by converting the signal sequence 131-2. The signal sequence 134-3 is obtained by converting the signal sequence 131-3. The signal sequence 134-4 is obtained by converting the signal sequence 131-4. The signal sequence 134-5 is obtained by converting the signal sequence 131-5. The signal sequence 135-1 is the same as the signal sequence 132-1. The signal sequence 135-2 is obtained by converting the signal sequence 132-2. The signal sequence 135-3 is obtained by converting the signal sequence 132-3. The signal sequence 135-4 is obtained by converting the signal sequence 132-4. The signal sequence 135-5 is obtained by converting the signal sequence 132-5.

In the first correlation analysis method, the analysis apparatus 100 averages the signal sequences 134-1 to 134-5 to generate a signal sequence 136-1 for one block. In addition, the analysis apparatus 100 averages the signal sequences 135-1 to 135-5 to generate a signal sequence 137-1 for one block. In the averaging, the average of a plurality of measured values at the same time on different days is computed. Each signal sequence 136-1 and 137-1 has a duration of 24 hours, which is the same as that of each signal sequence 134-1 to 134-5 and 135-1 to 135-5.

The analysis apparatus 100 computes a correlation coefficient in the time domain between the signal sequences 136-1 and 137-1. The correlation coefficient in the time domain is computed using the above-described expression (2). The analysis apparatus 100 determines the existence or absence of an inclusion relationship on the basis of the computed correlation coefficient.

For example, the analysis apparatus 100 determines that the signal sequence 131 includes the signal sequence 132 if the computed correlation coefficient exceeds a threshold. The analysis apparatus 100 may determine the existence or absence of the inclusion relationship on the basis of mutual comparison between the correlation coefficient with the signal sequence 131 and the correlation coefficients with the signal sequences on the other branch lines. If it is previously known that there is at least one branch line that is affected by the signal sequence 132, the analysis apparatus 100 determines that the signal sequence 131 includes the signal sequence 132 if the correlation coefficient between the signal sequences 131 and 132 is the maximum. In addition, if it is previously known that there is at least one branch line that is not affected by the signal sequence 132, the analysis apparatus 100 determines that the signal sequence 131 does not include the signal sequence 132 if the correlation coefficient between the signal sequences 131 and 132 is the minimum.

Figure 8:
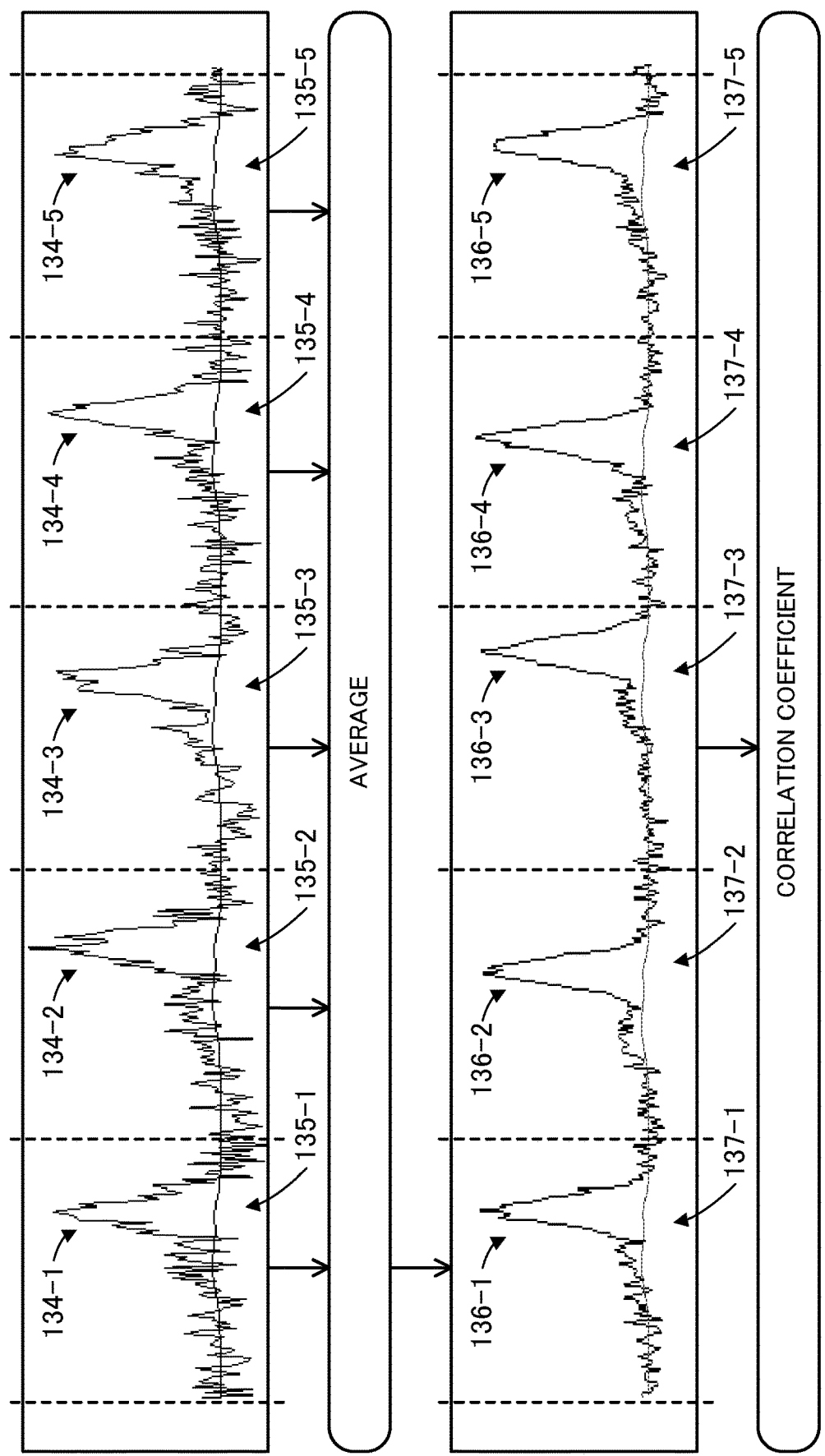
FIG. 8 illustrates a second example of correlation analysis.

FIG. 8 illustrates a second example of correlation analysis.

As in the first correlation analysis, in the second correlation analysis, the analysis apparatus 100 averages the signal sequences 134-1 to 134-5 to generate a signal sequence 136-1, and averages the signal sequences 135-1 to 135-5 to generate a signal sequence 137-1. In addition, the analysis apparatus 100 selects a different block as a base block, performs alignment for the new base block, and averages the signal sequences after the alignment.

More specifically, the analysis apparatus 100 selects the second day as a base block, and performs the alignment of FIG. 5 using the signal sequence 132-2 belonging to the selected base block as a base signal. Thereby, the alignment is performed on the signal sequences 132-1 and 132-3 to 132-5, and the alignment is performed on the signal sequences 131-1 and 131-3 to 131-5 with the corresponding warping functions. The analysis apparatus 100 then averages the alignment results of the signal sequences 131-1 to 131-5 to generate a signal sequence 136-2, and averages the alignment results of the signal sequences 132-1 to 132-5 to generate a signal sequence 137-2.

Similarly, the analysis apparatus 100 selects the third day as a base block, and performs the alignment of FIG. 5 using the signal sequence 132-3 as a base signal. The analysis apparatus 100 averages the alignment results of the signal sequences 131-1 to 131-5 to generate a signal sequence 136-3, and averages the alignment results of the signal sequences 132-1 to 132-5 to generate a signal sequence 137-3. The analysis apparatus 100 selects the fourth day as a base block, and performs the alignment of FIG. 5 using the signal sequence 132-4 as a base signal. The analysis apparatus 100 averages the alignment results of the signal sequences 131-1 to 131-5 to generate a signal sequence 136-4, and averages the alignment results of the signal sequences 132-1 to 132-5 to generate a signal sequence 137-4. The analysis apparatus 100 selects the fifth day as a base block, and performs the alignment of FIG. 5 using the signal sequence 132-5 as a base signal. The analysis apparatus 100 averages the alignment results of the signal sequences 131-1 to 131-5 to generate a signal sequence 136-5, and averages the alignment results of the signal sequences 132-1 to 132-5 to generate a signal sequence 137-5.

The analysis apparatus 100 connects thus generated signal sequences 136-1 to 136-5 to form a series of signal sequences. In addition, the analysis apparatus 100 connects thus generated signal sequences 137-1 to 137-5 to form a series of signal sequences. The analysis apparatus 100 computes a correlation coefficient in the time domain between the signal sequences 136-1 to 136-5 and the signal sequences 137-1 to 137-5. The correlation coefficient in the time domain is computed using the above-described expression (2). The analysis apparatus 100 determines the existence or absence of an inclusion relationship on the basis of the computed correlation coefficient.

As compared with the first correlation analysis, the second correlation analysis uses signal sequences with a long duration in the computation of the correlation coefficient and is less affected by the contingency of a base signal selected in the alignment. Thus, an improvement in the accuracy of the correlation analysis is expected.

Figure 9:
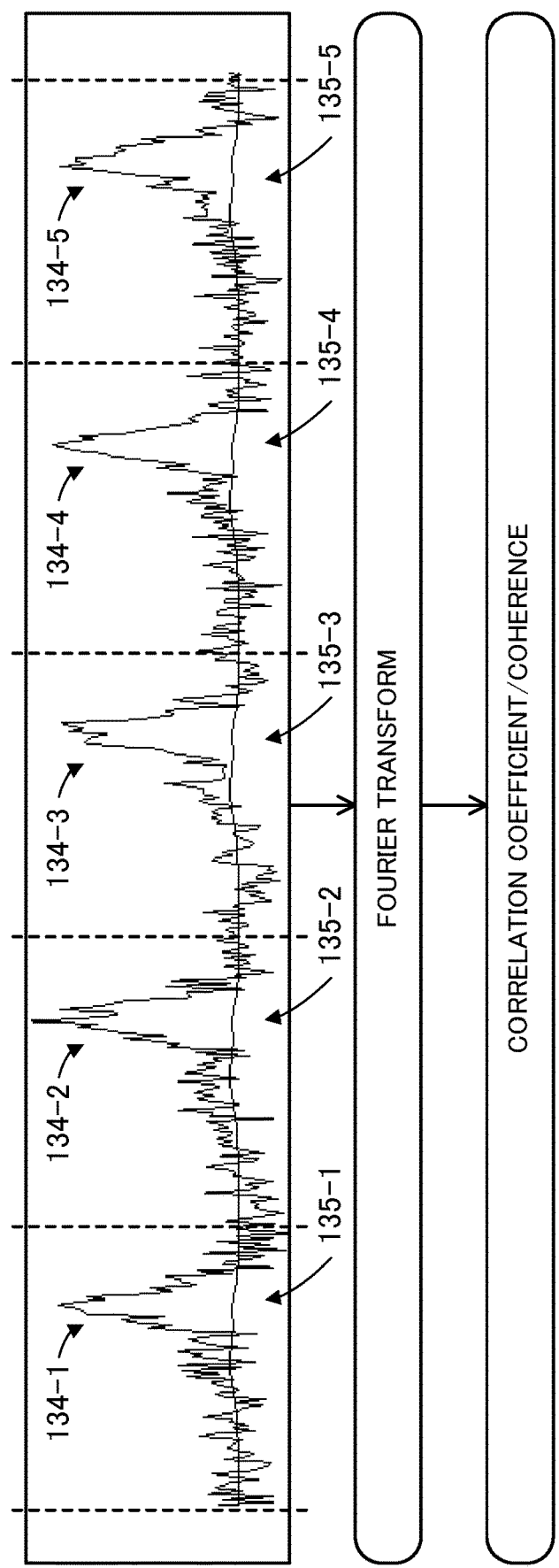
FIG. 9 illustrates a third example of correlation analysis.

FIG. 9 illustrates a third example of correlation analysis.

In the third correlation analysis, the analysis apparatus 100 connects the signal sequences 134-1 to 134-5 after alignment to form a series of signal sequences. In addition, the analysis apparatus 100 connects the signal sequences 135-1 to 135-5 after alignment to form a series of signal sequences. The analysis apparatus 100 then performs a discrete Fourier transform such as a fast Fourier transform (FFT) on the signal sequences 134-1 to 134-5 to compute the frequency spectrum of the target signal. In addition, the analysis apparatus 100 performs the discrete Fourier transform on the signal sequences 135-1 to 135-5 to compute the frequency spectrum of the reference signal.

The analysis apparatus 100 computes a correlation coefficient or coherence in the frequency domain between the frequency spectrum of the target signal and the frequency spectrum of the reference signal. The correlation coefficient in the frequency domain is computed using the above-described expression (3). The coherence is computed using the above-described expressions (4) and (5). The analysis apparatus 100 determines the existence or absence of an inclusion relationship on the basis of the computed correlation coefficient or coherence.

Figure 10:
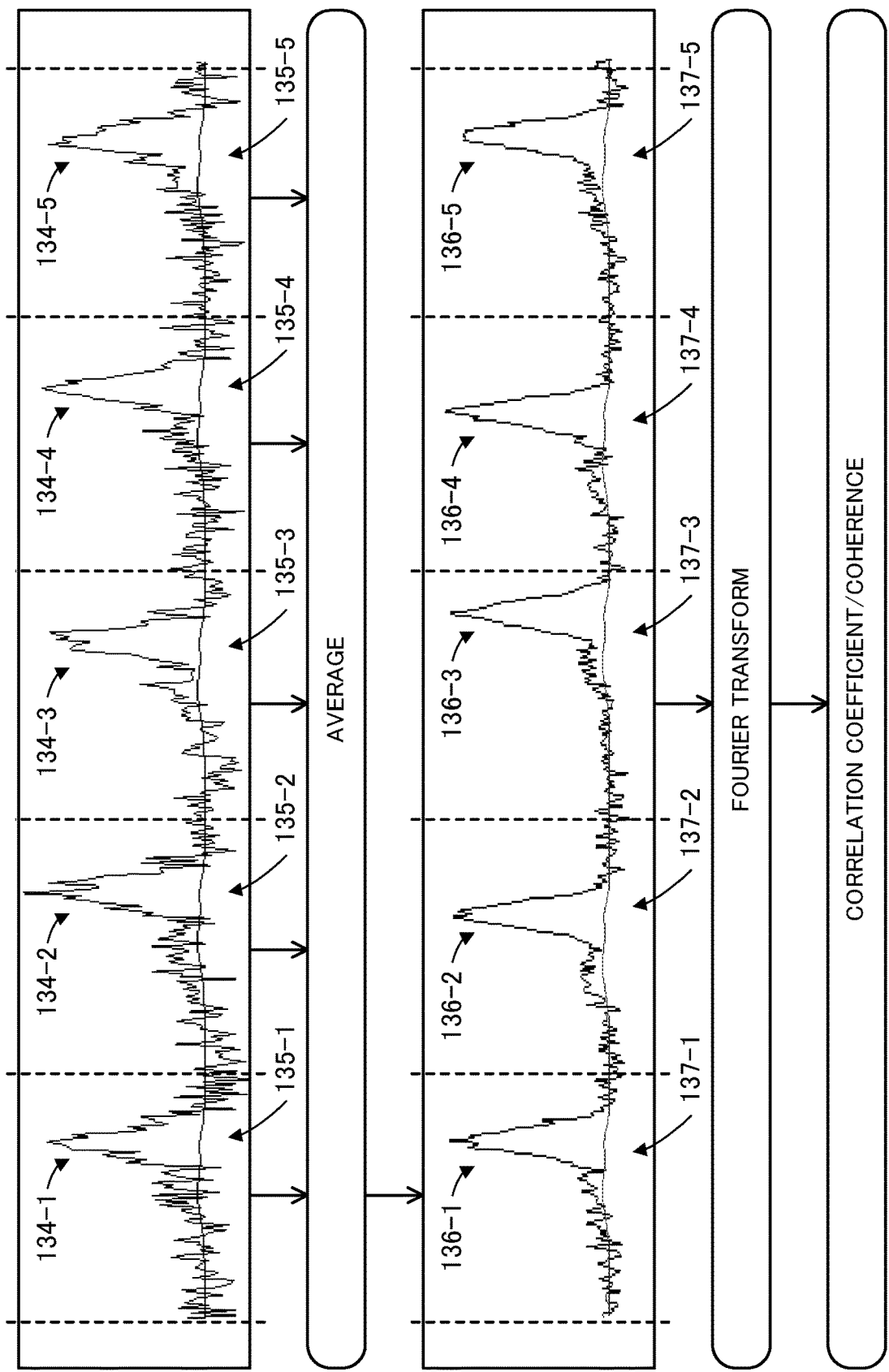
FIG. 10 illustrates a fourth example of correlation analysis.

FIG. 10 illustrates a fourth example of correlation analysis.

As in the second correlation analysis, in the fourth correlation analysis, the analysis apparatus 100 averages the signal sequences 134-1 to 134-5 to generate a signal sequence 136-1 and averages the signal sequences 135-1 to 135-5 to generate a signal sequence 137-1. In addition, as in the second correlation analysis, the analysis apparatus 100 generates average signal sequences 136-2 to 136-5 and average signal sequences 137-2 to 137-5. The analysis apparatus 100 connects the signal sequences 136-1 to 136-5 to form a series of signal sequences. In addition, the analysis apparatus 100 connects the signal sequences 137-1 to 137-5 to form a series of signal sequences.

The analysis apparatus 100 performs a discrete Fourier transform on the signal sequences 136-1 to 136-5 to compute the frequency spectrum of the target signal. In addition, the analysis apparatus 100 performs the discrete Fourier transform on the signal sequences 137-1 to 137-5 to compute the frequency spectrum of the reference signal. As in the third correlation analysis, the analysis apparatus 100 computes a correlation coefficient or coherence in the frequency domain between the frequency spectrum of the target signal and the frequency spectrum of the reference signal. The correlation coefficient in the frequency domain is computed using the above-described expression (3). The coherence is computed using the above-described expressions (4) and (5). The analysis apparatus 100 determines the existence or absence of an inclusion relationship on the basis of the computed correlation coefficient or coherence. As compared with the third correlation analysis, the fourth correlation analysis is less affected by the contingency of a base signal selected in the alignment. Thus, an improvement in the accuracy of the correlation analysis is expected.

The following additionally explains why the above-described first correlation analysis and second correlation analysis improve the accuracy of the correlation analysis. As seen in an expression (7), assume that the signal sequence g is expressed as the sum of a signal sequence obtained by attenuating the signal sequence f at an attenuation rate a and a noise sequence n. The attenuation rate a is zero or greater and is sufficiently less than one. It is also assumed that the warping function $\gamma_i$ for the i-th block (i=1, ..., M) is to convert the time t into the time $\gamma_i(t)$. In this case, the alignment result of the signal sequence g is represented as an expression (8). Then, the signal sequence h obtained by averaging the alignment results for the M blocks is defined as an expression (9). In the expression (9), the first item on the right side is a signal item and the second item on the right side is a noise item.

$$g(t) = af(t) + n(t) \text{ where } 0 \leq a \ll 1 \quad (7)$$

$$g_i(\gamma_i(t)) = af_i(\gamma_i(t)) + n_i(\gamma_i(t)) \quad (8)$$

$$h(t) = \frac{1}{M}\sum_{i=1}^{M} g_i(\gamma_i(t)) = \frac{a}{M}\sum_{i=1}^{M} f_i(\gamma_i(t)) + \frac{1}{M}\sum_{i=1}^{M} n_i(\gamma_i(t)) \quad (9)$$

As an index for noise suppression effect, a peak signal to noise ratio (PNR) is considered, which is obtained by dividing the peak (maximum value) of the signal item by the standard deviation of the noise item. Assume that the noise sequence n is Gaussian noise and follows a normal distribution. For simple explanation, assume that the M blocks have the same maximum signal level. The peak signal to noise ratio $PNR_g$ of the signal sequence g before alignment is computed from an expression (10). In addition, assuming that the standard deviation of the noise item does not change before and after the alignment, the peak signal to noise ratio PNR) of the signal sequence h after the alignment and averaging is computed from an expression (11). In the signal sequence h, noise is cancelled out by the averaging and the standard deviation of the noise item is reduced to $1/M^{0.5}$.

$$PNR_g = \frac{a\max_t(f_i(t))}{\sigma} \sim \frac{a\max_t(f(t))}{\sigma} \quad (10)$$

$$PNR_h = \frac{\frac{a}{M}\sum_{i=1}^{M}\max_t(f_i(\gamma_i(t)))}{\sigma/\sqrt{M}} \sim \frac{a\sqrt{M}\max_t(f(t))}{\sigma} \quad (11)$$

As seen in the above expressions (10) and (11), the first correlation analysis and second correlation analysis are expected to mitigate the effect of noise and improve the peak signal to noise ratio, and thus to improve the accuracy of correlation analysis.

The following additionally explains why the above-described third correlation analysis and fourth correlation analysis improve the accuracy of correlation analysis. As compared with the case where a signal sequence does not contain a phase noise, the frequency spectrum of a signal sequence containing a phase noise has high frequency components other than the center frequency. In the case where the phase noise is a random noise, the frequency spectrum has a wide range. In the case where the phase noise has specific periodicity, secondary peaks appear at frequencies around the center frequency.

In view of this point, the third correlation analysis and fourth correlation analysis are able to improve the periodicity of a target signal and reference signal. Therefore, the frequency spectrum of the target signal and the frequency spectrum of the reference signal each have a narrow range. As a result, in the case where these signals have an inclusion relationship, the correlation coefficient or coherence between the two frequency spectrums is remarkably high, which reduces the risk of erroneous determination of the inclusion relationship.

The following describes the functions of the analysis apparatus 100.

Figure 11:
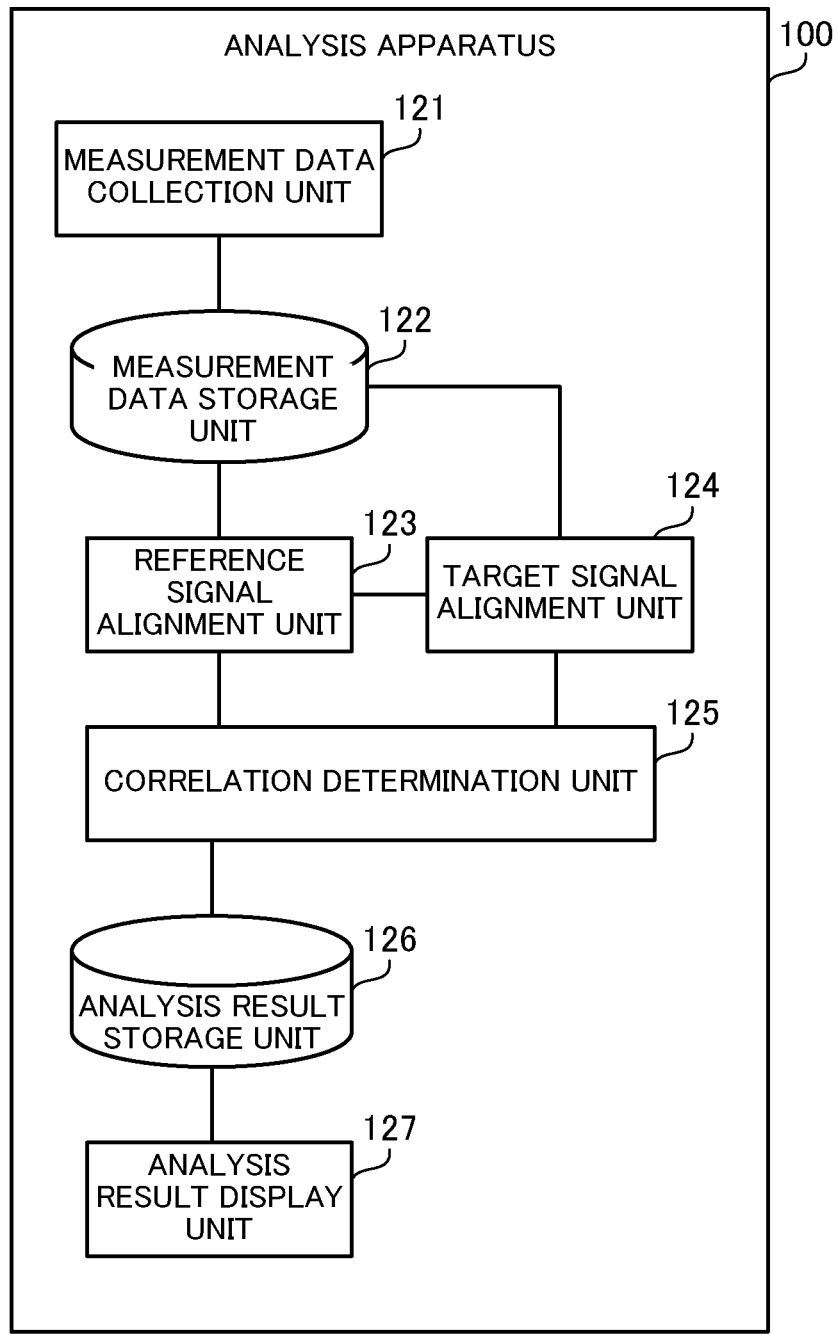
FIG. 11 is a block diagram illustrating an example of functions of an analysis apparatus.

FIG. 11 is a block diagram illustrating an example of functions of an analysis apparatus.

The analysis apparatus 100 includes a measurement data collection unit 121, a measurement data storage unit 122, a reference signal alignment unit 123, a target signal alignment unit 124, a correlation determination unit 125, an analysis result storage unit 126, and an analysis result display unit 127. The measurement data storage unit 122 and analysis result storage unit 126 are implemented by using the storage space of the RAM 102 or HDD 103, for example. The measurement data collection unit 121, reference signal alignment unit 123, target signal alignment unit 124, correlation determination unit 125, and analysis result display unit 127 are implemented by using a program to be executed by the CPU 101, for example.

The measurement data collection unit 121 collects measurement data obtained by the measurement devices 31, 32, 33, 34, 35, and 36 and stores it in the measurement data storage unit 122. For example, the measurement data collection unit 121 continuously receives measurement data from the measurement devices 31, 32, 33, 34, 35, and 36. The measurement data storage unit 122 stores therein the measurement data indicating measured values obtained by the measurement devices 31, 32, 33, 34, 35, and 36.

The reference signal alignment unit 123 selects the measurement data obtained by one of the measurement devices 31, 32, and 33 on the branch lines as a reference signal. The reference signal is specified by a user, for example. The reference signal alignment unit 123 divides the reference signal into a plurality of blocks with a duration of 24 hours and selects one block as a base block. The reference signal alignment unit 123 then performs alignment to expand or compress the reference signal of each of the other blocks in the time direction to match the reference signal of the base block, according to an algorithm such as the DTW. Through this alignment, a warping function for each block is generated.

The target signal alignment unit 124 selects the measurement data obtained by one of the measurement devices 34, 35, and 36 on the main lines as a target signal. The target signal alignment unit 124 divides the target signal into a plurality of blocks with a duration of 24 hours and obtains the warping functions from the reference signal alignment unit 123. The target signal alignment unit 124 performs alignment to expand or compress the target signal of each of the blocks in the time direction using the same warping function as used by the reference signal alignment unit 123.

The correlation determination unit 125 obtains the aligned reference signal from the reference signal alignment unit 123 and also obtains the aligned target signal from the target signal alignment unit 124. The correlation determination unit 125 performs correlation analysis between the aligned reference signal and the aligned target signal. For example, the correlation determination unit 125 computes a correlation coefficient through the correlation analysis in the time domain. Alternatively, for example, the correlation determination unit 125 computes a correlation coefficient or coherence through the correlation analysis in the frequency domain. The correlation analysis method is specified by the user, for example.

The correlation determination unit 125 then determines the existence or absence of an inclusion relationship in which the target signal includes the reference signal, on the basis of an index value such as a correlation coefficient or coherence. As the correlation is higher, the possibility of existence of the inclusion relationship increases, and vice versa. For example, the correlation determination unit 125 determines that a target signal associated with an index value exceeding a threshold has an inclusion relationship with the reference signal. Alternatively, for example, the correlation determination unit 125 compares index values computed for a plurality of target signals with one another, and determines that a target signal associated with the maximum index value has an inclusion relationship with the reference signal. Yet alternatively, for example, the correlation determination unit 125 compares the index values computed for the plurality of target signals with one another, and determines that a target signal associated with the minimum index value does not have an inclusion relationship with the reference signal. The correlation determination unit 125 stores analysis result data indicating the result of the correlation analysis in the analysis result storage unit 126.

The analysis result storage unit 126 stores therein the analysis result data. The analysis result data includes, for example, an index value such as a computed correlation coefficient or coherence. In addition, the analysis result data includes, for example, aligned target signals and aligned reference signals. In addition, the analysis result data includes, for example, a result of determining an inclusion relationship. The analysis result display unit 127 displays, on the display device 111, the analysis result data stored in the analysis result storage unit 126. In this connection, the analysis result display unit 127 may transmit the analysis result data to another information processing apparatus.

FIG. 12 illustrates an example of a measurement data table.

The measurement data table 128 is stored in the measurement data storage unit 122. The measurement data table 128 has the following columns: Device ID, Time, and Measured Value. The Device ID column contains an identifier identifying a measurement device. The Time column contains the calculation time of a measured value by the measurement device. The Measured Value column contains the measured value of a physical quantity such as current.

FIG. 13 illustrates an example of a warping function table.

The warping function table 129 is created by the reference signal alignment unit 123. The warping function table 129 registers therein a warping function for each block. The warping function depends on a block. The warping function is to convert a time point within the same block. The time point is, for example, one of discrete time points obtained by dividing 24 hours into ten-minute increments. A single time point before alignment is mapped to a single time point after alignment.

The following describes how the analysis apparatus 130 operates. The following describes the above-described four correlation analysis methods. One of these four correlation analysis methods is selectively executed.

Figure 14:
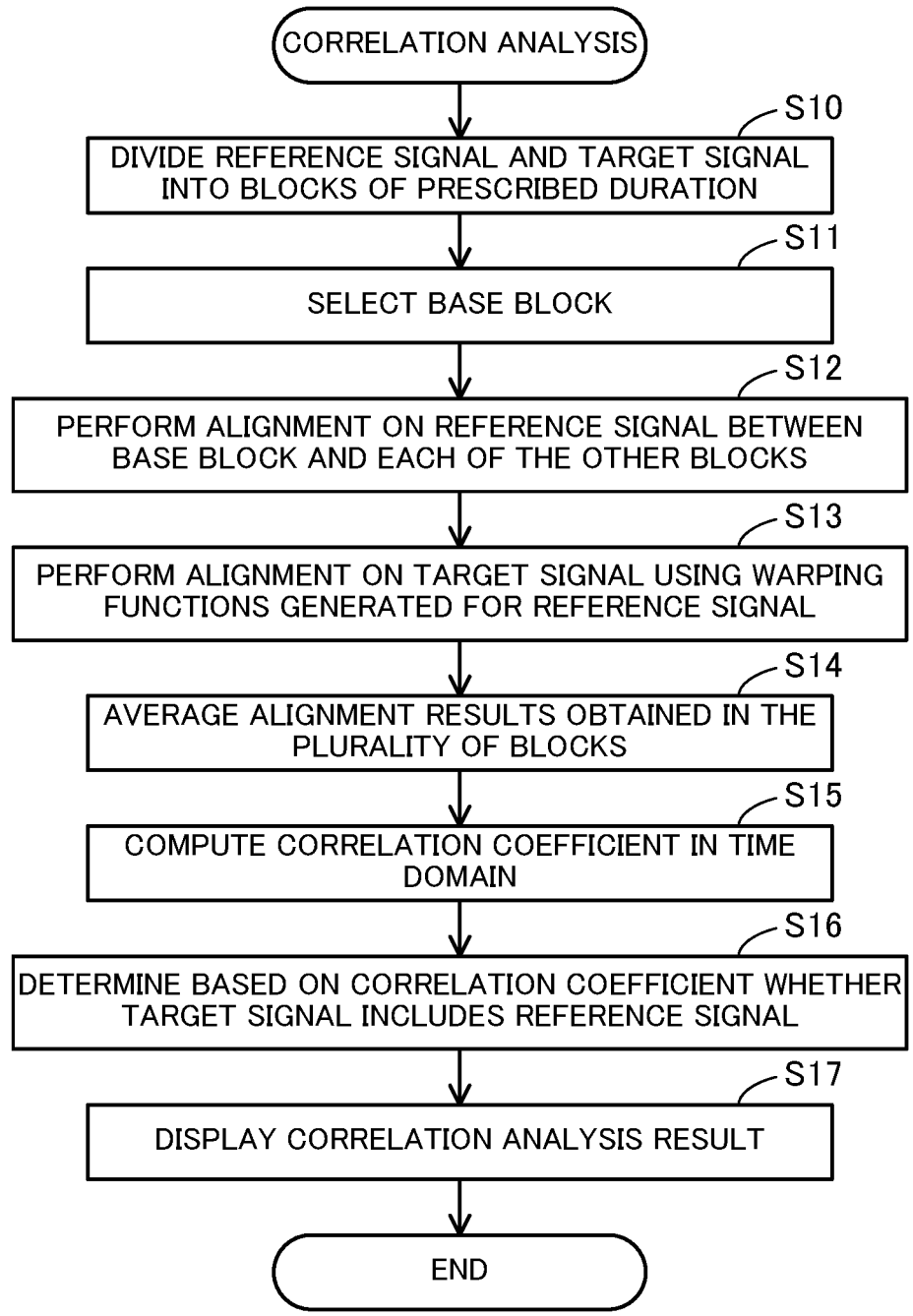
FIG. 14 is a flowchart illustrating an example of a first correlation analysis procedure.

FIG. 14 is a flowchart illustrating an example of a first correlation analysis procedure.

(S10) The reference signal alignment unit 123 divides a reference signal into blocks of prescribed duration (for example, 24-hour duration). The target signal alignment unit 124 divides a target signal into blocks of the prescribed duration.

(S11) The reference signal alignment unit 123 selects a base block. For example, the reference signal alignment unit 123 selects the beginning block as a base block.

(S12) The reference signal alignment unit 123 performs alignment on the reference signal between the base block and each of the other blocks. Here, the reference signal alignment unit 123 expands or compresses the reference signal of each of the other blocks in the time direction so that the reference signal of the block is similar to the reference signal of the base block. By doing so, a warping function is generated for each of the plurality of blocks.

(S13) The target signal alignment unit 124 performs alignment on the target signal for each of the plurality of blocks using the warping functions generated at step S12. Here, the target signal alignment unit 124 expands or compresses the target signal in the time direction in the same way as the reference signal.

(S14) The correlation determination unit 125 averages the aligned reference signals of the plurality of blocks, obtained at step S12. In addition, the correlation determination unit 125 averages the aligned target signals of the plurality of blocks, obtained at step S13.

(S15) The correlation determination unit 125 computes a correlation coefficient in the time domain between the average reference signal and the average target signal, generated at step S14.

(S16) The correlation determination unit 125 determines the existence or absence of an inclusion relationship, in which the target signal includes the reference signal, based on the correlation coefficient computed at step S15.

(S17) The analysis result display unit 127 displays the correlation analysis result on the display device 111. For example, the correlation coefficient and the existence or absence of the inclusion relationship are displayed.

Figure 15:
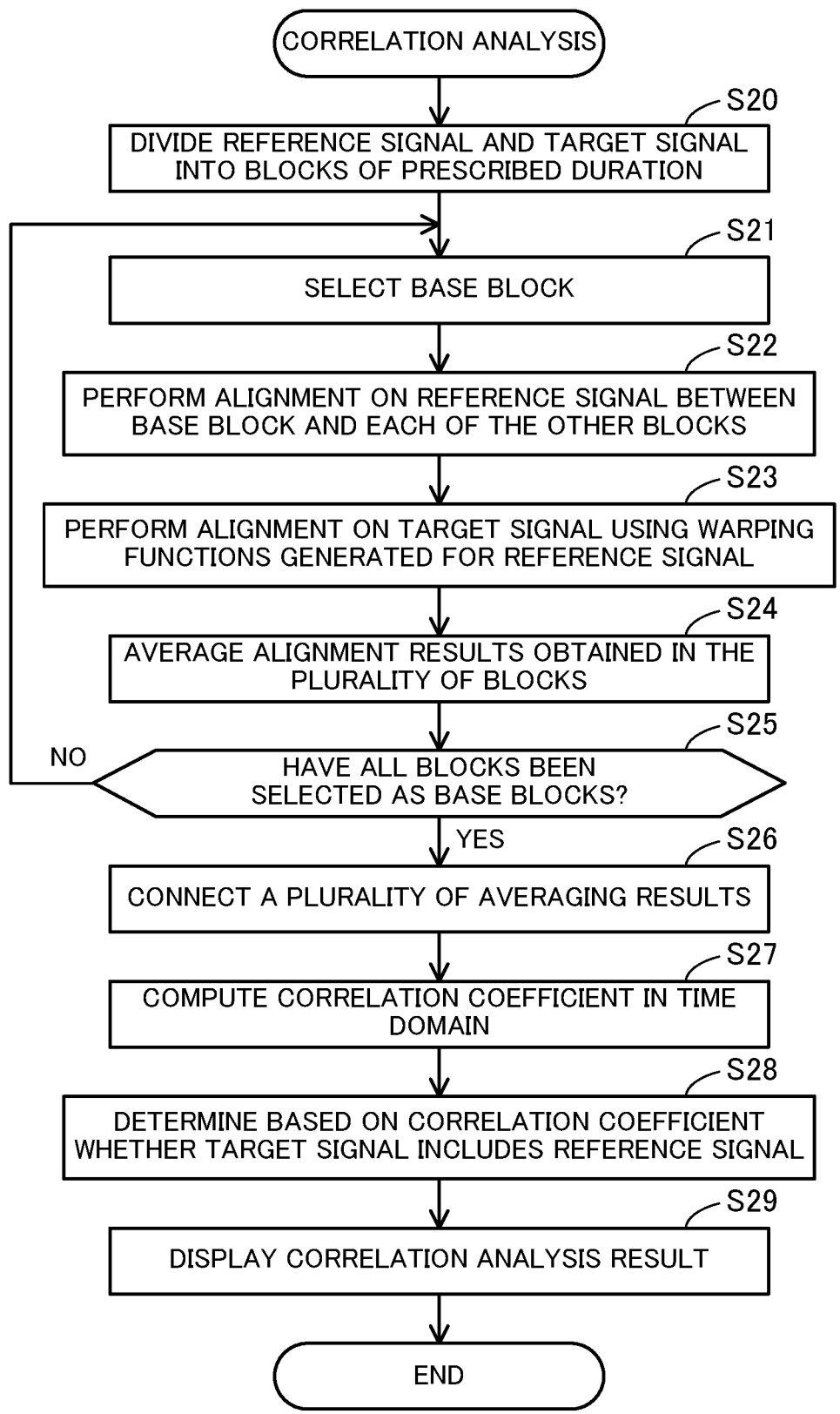
FIG. 15 is a flowchart illustrating an example of a second correlation analysis procedure.

FIG. 15 is a flowchart illustrating an example of a second correlation analysis procedure.

(S20) The reference signal alignment unit 123 divides a reference signal into blocks of prescribed duration. The target signal alignment unit 124 divides a target signal into blocks of the prescribed duration.

(S21) The reference signal alignment unit 123 selects one block as a base block.

(S22) The reference signal alignment unit 123 performs alignment on the reference signal between the base block and each of the other blocks. Here, the reference signal alignment unit 123 expands or compresses the reference signal of each block in the time direction so that the reference signal of the block is similar to the reference signal of the base block. By doing so, a warping function is generated for each of the plurality of blocks.

(S23) The target signal alignment unit 124 performs alignment on the target signal for each of the plurality of blocks using the warping functions generated at step S22. Here, the target signal alignment unit 124 expands or compresses the target signal in the time direction in the same manner as the reference signal.

(S24) The correlation determination unit 125 averages the aligned reference signals of the plurality of blocks, obtained at step S22. In addition, the correlation determination unit 125 averages the aligned target signals of the plurality of blocks, obtained at step S23.

(S25) The correlation determination unit 125 determines whether all blocks have been selected as base blocks. If all the blocks have been selected as base blocks, the process proceeds to step S26. Otherwise, the process proceeds back to step S21.

(S26) The correlation determination unit 125 connects the average reference signals generated by executing steps S21 to S25 plural times. In addition, the correlation determination unit 125 connects the average target signals generated by executing steps S21 to S25 plural times.

(S27) The correlation determination unit 125 computes a correlation coefficient in the time domain between the connected average reference signals and the connected average target signals, generated at step S26.

(S28) The correlation determination unit 125 determines the existence or absence of an inclusion relationship in which the target signal includes the reference signal, on the basis of the correlation coefficient computed at step S27.

(S29) The analysis result display unit 127 displays the correlation analysis result on the display device 111. For example, the correlation coefficient and the existence or absence of the inclusion relationship are displayed.

Figure 16:
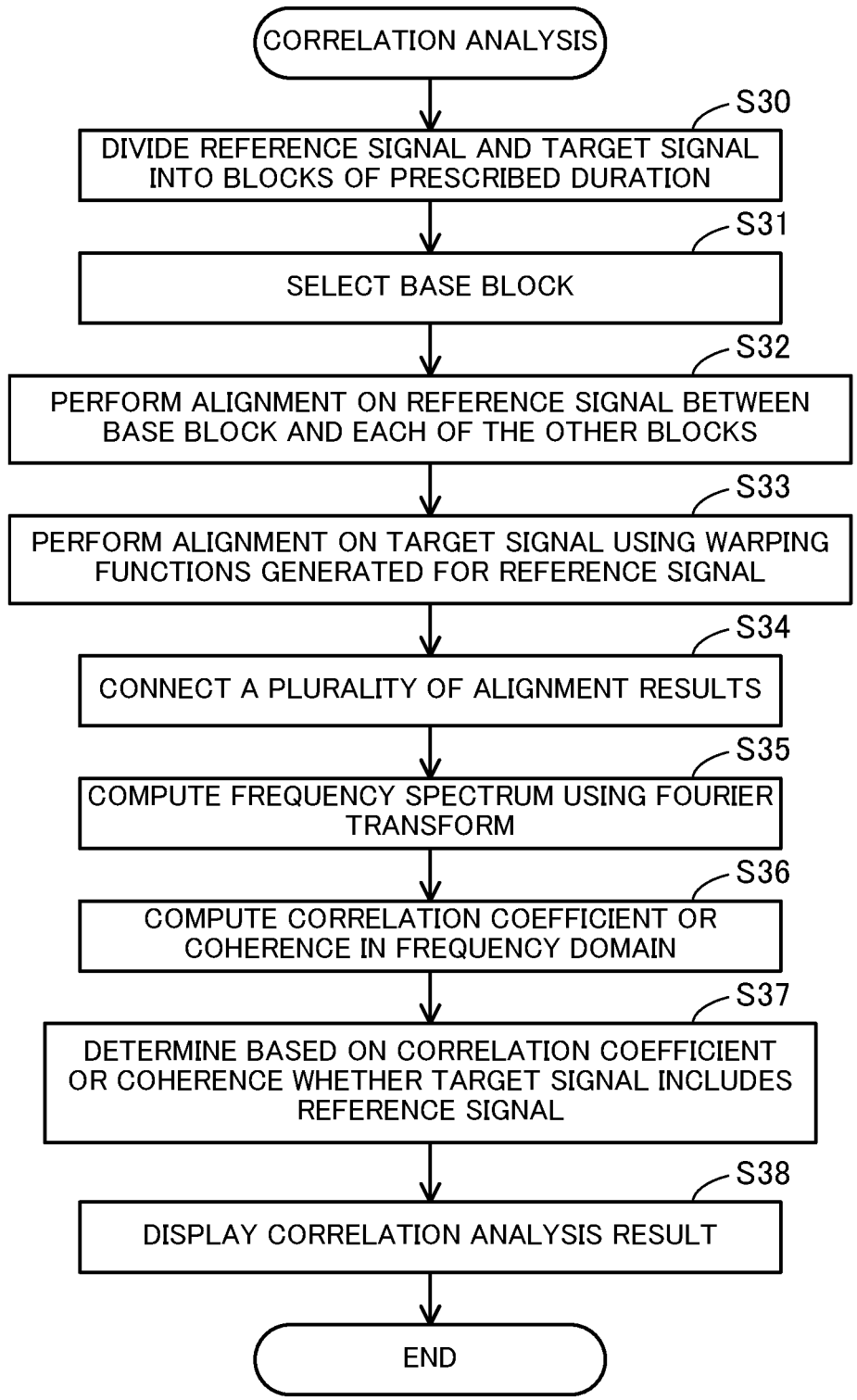
FIG. 16 is a flowchart illustrating an example of a third correlation analysis procedure.

FIG. 16 is a flowchart illustrating an example of a third correlation analysis procedure.

(S30) The reference signal alignment unit 123 divides a reference signal into blocks of prescribed duration. The target signal alignment unit 124 divides a target signal into blocks of the prescribed duration.

(S31) The reference signal alignment unit 123 selects a base block. For example, the reference signal alignment unit 123 selects the beginning block as a base block.

(S32) The reference signal alignment unit 123 performs alignment on the reference signal between the base block and each of the other blocks. Here, the reference signal alignment unit 123 expands or compresses the reference signal of each of the other blocks in the time direction so that the reference signal of the block is similar to the reference signal of the base block. By doing so, a warping function is generated for each of the plurality of blocks.

(S33) The target signal alignment unit 124 performs alignment on the target signal for each of the plurality of blocks using the warping functions generated at step S32. Here, the target signal alignment unit 124 expands or compresses the target signal in the time direction in the same manner as the reference signal.

(S34) The correlation determination unit 125 connects the aligned reference signals of the plurality of blocks, obtained at step S32. In addition, the correlation determination unit 125 connects the aligned target signals of the plurality of blocks, obtained at step S33.

(S35) The correlation determination unit 125 performs a Fourier transform on the connected aligned reference signals generated at step S34 to compute the frequency spectrum of the reference signal. In addition, the correlation determination unit 125 performs the Fourier transform on the connected aligned target signal generated at step S34 to compute the frequency spectrum of the target signal.

(S36) The correlation determination unit 125 computes a correlation coefficient in the frequency domain between the frequency spectrum of the reference signal and the frequency spectrum of the target signal, computed at step S35. Alternatively, the correlation determination unit 125 computes a coherence in the frequency domain.

(S37) The correlation determination unit 125 determines the existence or absence of an inclusion relationship in which the target signal includes the reference signal, on the basis of the correlation coefficient or coherence computed at step S36.

(S38) The analysis result display unit 127 displays the correlation analysis result on the display device 111. For example, the correlation coefficient or coherence and the existence or absence of the inclusion relationship are displayed.

Figure 17:
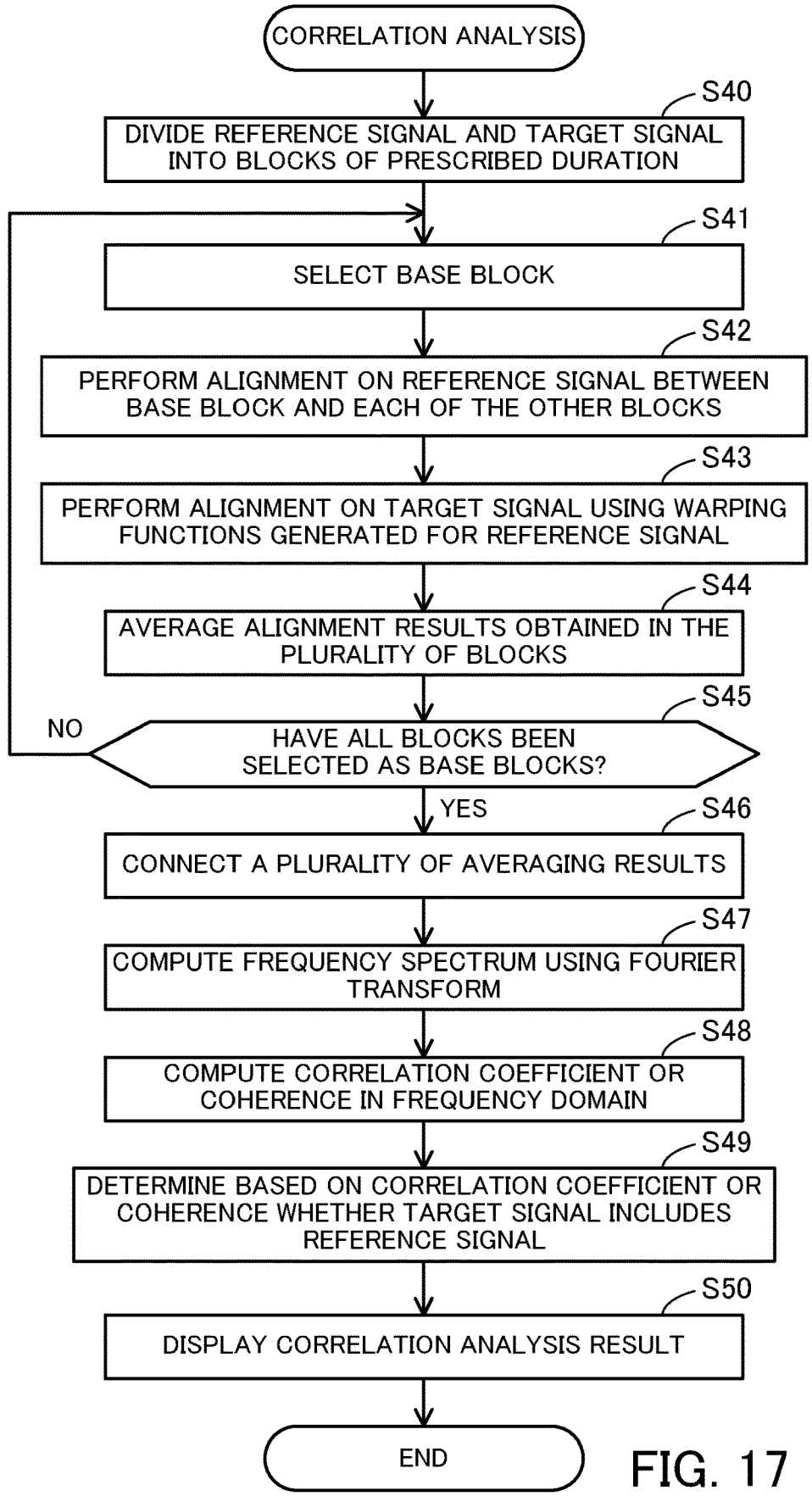
FIG. 17 is a flowchart illustrating an example of a fourth correlation analysis procedure.

FIG. 17 is a flowchart illustrating an example of a fourth correlation analysis procedure.

(S40) The reference signal alignment unit 123 divides a reference signal into blocks of prescribed duration. The target signal alignment unit 124 divides a target signal into blocks of the prescribed duration.

(S41) The reference signal alignment unit 123 selects one block as a base block.

(S42) The reference signal alignment unit 123 performs alignment on the reference signal between the base block and each of the other blocks. Here, the reference signal alignment unit 123 expands or compresses the reference signal of each of the other blocks in the time direction so that the reference signal of the block is similar to the reference signal of the base block. By doing so, a warping function is generated for each of the plurality of blocks.

(S43) The target signal alignment unit 124 performs alignment on the target signal for each of the plurality of blocks using the warping functions generated at step S42. Here, the target signal alignment unit 124 expands or compresses the target signal in the time direction in the same manner as the reference signal.

(S44) The correlation determination unit 125 averages the aligned reference signals of the plurality of blocks, obtained at step S42. In addition, the correlation determination unit 125 averages the aligned target signals of the plurality of blocks, obtained at step S43.

(S45) The correlation determination unit 125 determines whether all blocks have been selected as base blocks. If all the blocks have been selected as base blocks, the process proceeds to step S46. Otherwise, the process proceeds back to step S41.

(S46) The correlation determination unit 125 connects the average reference signals generated by executing steps S41 to S45 plural times. In addition, the correlation determination unit 125 connects the average target signals generated by executing steps S41 to S45 plural times.

(S47) The correlation determination unit 125 performs a Fourier transform on the connected average reference signals generated at step S46 to compute the frequency spectrum of the reference signal. In addition, the correlation determination unit 125 performs the Fourier transform on the connected average target signals generated at step S46 to compute the frequency spectrum of the target signal.

(S48) The correlation determination unit 125 computes a correlation coefficient in the frequency domain between the frequency spectrum of the reference signal and the frequency spectrum of the target signal, computed at step S47. Alternatively, the correlation determination unit 125 computes a coherence in the frequency domain.

(S49) The correlation determination unit 125 determines the existence or absence of an inclusion relationship in which the target signal includes the reference signal, on the basis of the correlation coefficient or coherence computed at step S48.

(S50) The analysis result display unit 127 displays the correlation analysis result on the display device 111. For example, the correlation coefficient or coherence and the existence or absence of the inclusion relationship are displayed.

Figure 18:
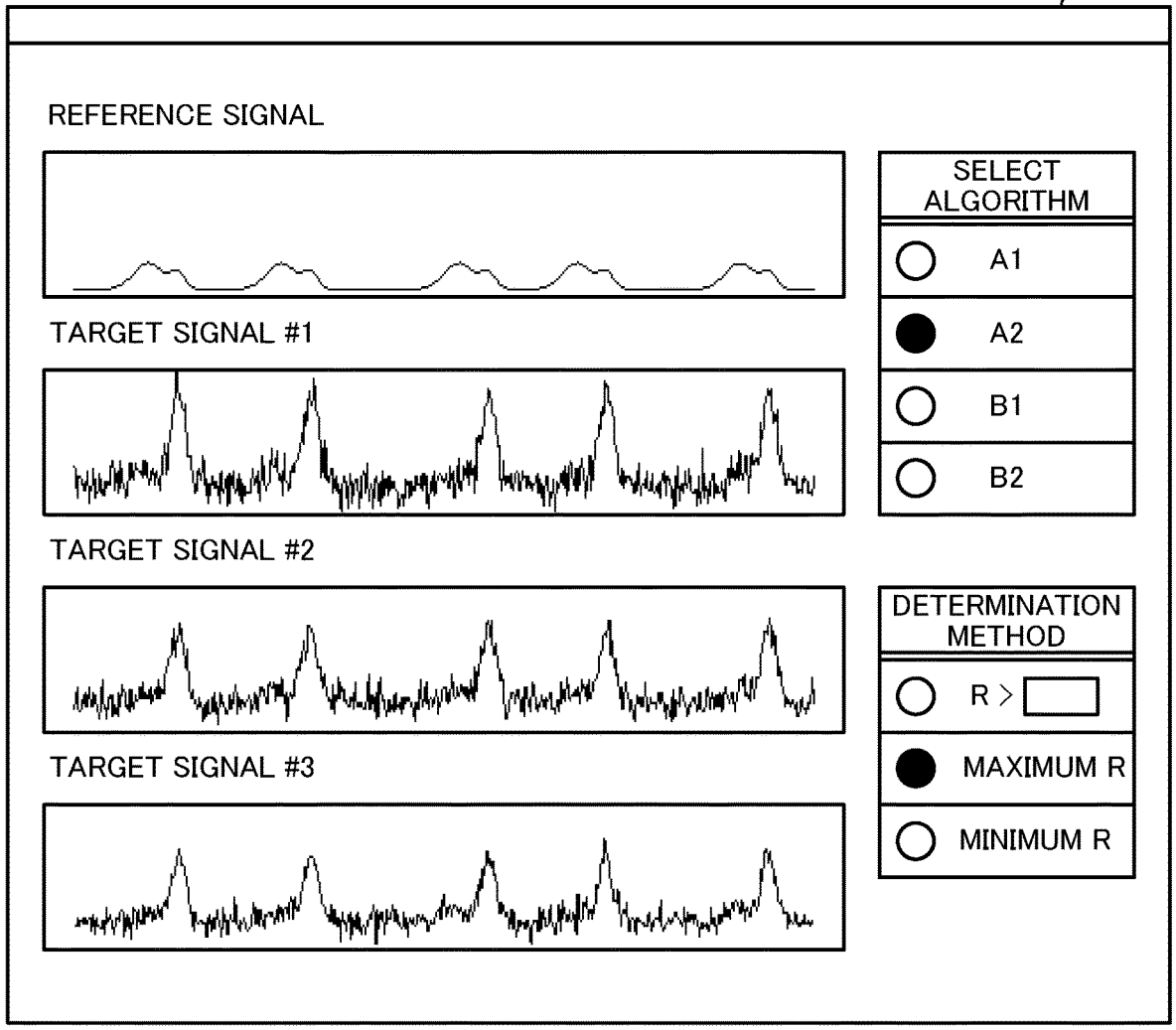
FIG. 18 illustrates a first example of a correlation analysis screen.

FIG. 18 is a first example of a correlation analysis screen.

The correlation analysis screen 151 is displayed on the display device 111. The correlation analysis screen 151 displays a reference signal representing measured values obtained by one measurement device on a branch line. In addition, the correlation analysis screen 151 displays target signals #1, #2, and #3 representing measured values obtained by the measurement devices 34, 35, and 36 on main lines. The user is able to select a correlation analysis algorithm on the correlation analysis screen 151. The above-described four correlation analysis methods are options for a correlation analysis algorithm. In addition, the user is able to select a method for determination of an inclusion relationship on the correlation analysis screen 151. There are the following three options for a method of determining an inclusion relationship: an index value such as a correlation coefficient or coherence exceeds a threshold; an index value is the maximum; and an index value is the minimum. The user may be allowed to enter the threshold for the index value.

Figure 19:
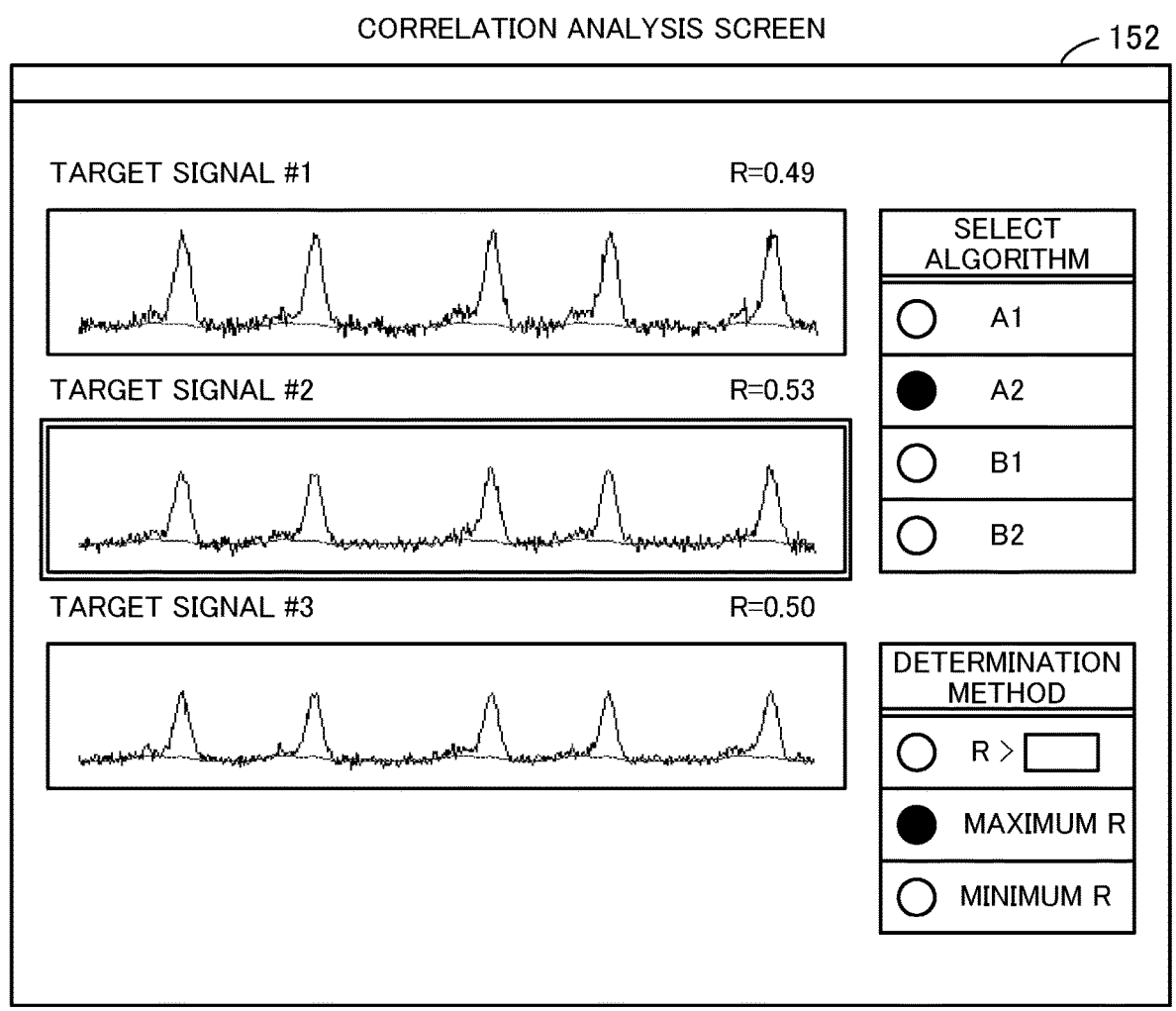
FIG. 19 illustrates a second example of a correlation analysis screen.

FIG. 19 illustrates a second example of a correlation analysis screen.

The correlation analysis screen 152 is displayed on the display device 111 after the correlation analysis screen 151. The correlation analysis screen 152 displays the target signals #1, #2, and #3 in the time domain obtained after alignment and averaging. In addition, the correlation analysis screen 152 superimposes and displays the reference signal in the time domain obtained after the alignment and averaging, on the target signals #1, #2, and #3. In addition, the correlation analysis screen 152 displays an index value such as a correlation coefficient or coherence computed for each target signal #1, #2, and #3.

The correlation analysis screen 152 displays a determination result of an inclusion relationship. In the case where a selected determination method has a condition that an index value exceeds a threshold, target signals having inclusion relationships with the reference signal are displayed in highlight. In the case where the selected determination method has a condition that an index value is the maximum, one target signal having an inclusion relationship with the reference signal is displayed in highlight. For example, assuming that the target signal #1 has a correlation coefficient of 0.49, the target signal #2 has a correlation coefficient of 0.53, and the target signal #3 has a correlation coefficient of 0.50, the target signal #2 is determined as having an inclusion relationship with the reference signal and is displayed in highlight. In the case where the selected determination method has a condition that an index value is the minimum, one target signal that does not have an inclusion relationship with the reference signal is displayed in highlight.

With the analysis apparatus 100 of the second embodiment, the strength of a correlation between a target signal and a reference signal is evaluated with correlation analysis, and an inclusion relationship in which the reference signal is contained in the target signal is inferred according to the strength of the correlation. Therefore, it becomes possible to provide analysis results useful for various measures such as maintenance in wiring, change in wiring, and change in arrangement of machines. In addition, as preprocessing of the correlation analysis, alignment is performed to expand or compress the target signal and reference signal in the time direction. As a result, in the case where an inclusion relationship exists, an index value such as a correlation coefficient becomes sufficiently high, which improves the accuracy of determining the inclusion relationship. That is, the difference in index value increases between the case where the inclusion relationship exists and the case where no inclusion relationship exists. Thus, a risk of erroneous determination is reduced.

In addition, using the almost periodicity of the target signal and reference signal, indirect alignment is performed in such a way that the reference signal is expanded or compressed between different measurement days and then this expansion or compression method is applied to the target signal. Therefore, even if the target signal has a lot of noise, alignment is performed with high accuracy in the case where an inclusion relationship exists, as compared with direct alignment in which one of the target signal and reference signal is made to match the other. As a result, in the case where the inclusion relationship exists, an index value such as a correlation coefficient becomes sufficiently high, which improves the accuracy of determining the inclusion relationship.

In this connection, since a target signal measured on a main line is affected by a number of branch lines, the target signal contains a lot of components that are not synchronized with a reference signal measured on a specific branch line. Therefore, the target signal appears to contain a lot of noise in view of the reference signal. If the target signal has a lot of noise, the direct alignment may fail to accurately match the target signal to the reference signal, and therefore there is a high risk of obtaining an erroneous alignment result. By contrast, the indirect alignment utilizing the almost periodicity makes it possible to improve the alignment accuracy.

According to one aspect, an accuracy of determining an inclusion relationship between two time-series data sets is improved.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A non-transitory computer-readable storage medium storing a program that causes a computer to execute a process comprising:
    obtaining a first time-series data set indicating first measured values obtained by a first device during a plurality of periods including a first period and a second period and a second time-series data set indicating second measured values obtained by a second device during the plurality of periods;
    performing first alignment to convert positions in a time domain of first measured values belonging to the second period, based on first measured values belonging to the first period;
    performing second alignment to convert positions in the time domain of second measured values belonging to the second period, based on a correspondence relationship between positions before and after conversion of the first alignment;
    performing correlation analysis between a third time-series data set obtained by converting the first time-series data set using the first alignment and a fourth time-series data set obtained by converting the second time-series data set using the second alignment; and
    determining existence or absence of an inclusion relationship, based on a result of the correlation analysis, the inclusion relationship indicating that the second measured values contain a component of the first measured values.

2. The non-transitory computer-readable storage medium according to claim 1, wherein:
    the plurality of periods further include a third period;
    the first alignment includes converting positions of first measured values belonging to the third period, based on the first measured values belonging to the first period;
    the correspondence relationship obtained for the second period is different from a correspondence relationship obtained for the third period; and
    the second alignment includes converting the positions of the second measured values belonging to the second period, based on the correspondence relationship obtained for the second period, and converting positions of second measured values belonging to the third period, based on the correspondence relationship obtained for the third period.

3. The non-transitory computer-readable storage medium according to claim 1, wherein the correlation analysis includes
    generating a first average data set by averaging first measured values included in the third time-series data set over the plurality of periods and a second average data set by averaging second measured values included in the fourth time-series data set over the plurality of periods, and computing a correlation index value between the first average data set and the second average data set.

4. The non-transitory computer-readable storage medium according to claim 1, wherein:
the process further includes
performing third alignment to convert positions in the time domain of the first measured values belonging to the first period, based on the first measured values belonging to the second period, and
performing fourth alignment to convert positions in the time domain of second measured values belonging to the first period, based on a correspondence relationship between positions before and after conversion of the third alignment; and
the correlation analysis includes
generating a first average data set by averaging first measured values included in the third time-series data set over the plurality of periods, a second average data set by averaging second measured values included in the fourth time-series data set over the plurality of periods, a third average data set by averaging, over the plurality of periods, first measured values included in a fifth time-series data set obtained by converting the first time-series data set using the third alignment, and a fourth average data set by averaging, over the plurality of periods, second measured values included in a sixth time-series data set obtained by converting the second time-series data set using the fourth alignment, and
computing a correlation index value between a first connected data set obtained by connecting the first average data set and the third average data set in the time domain and a second connected data set obtained by connecting the second average data set and the fourth average data set in the time domain.

5. The non-transitory computer-readable storage medium according to claim 1, wherein the correlation analysis includes
computing, using a Fourier transform, a first frequency spectrum from the third time-series data set and a second frequency spectrum from the fourth time-series data set, and
computing a correlation index value between the first frequency spectrum and the second frequency spectrum.

6. The non-transitory computer-readable storage medium according to claim 1, wherein:
the process further includes
performing third alignment to convert positions in the time domain of the first measured values belonging to the first period, based on the first measured values belonging to the second period, and
performing fourth alignment to convert positions in the time domain of second measured values belonging to the first period, based on a correspondence relationship between positions before and after conversion of the third alignment; and
the correlation analysis includes
generating a first average data set by averaging first measured values included in the third time-series data set over the plurality of periods, a second average data set by averaging second measured values included in the fourth time-series data set over the plurality of periods, a third average data set by averaging, over the plurality of periods, first measured values included in a fifth time series data set obtained by converting the first time-series data set using the third alignment, and a fourth average data set by averaging, over the plurality of periods, second measured values included in a sixth time-series data set obtained by converting the second time-series data set using the fourth alignment,
computing, using a Fourier transform, a first frequency spectrum from a first connected data set obtained by connecting the first average data set and the third average data set in the time domain and a second frequency spectrum from a second connected data set obtained by connecting the second average data set and the fourth average data set in the time domain, and
computing a correlation index value between the first frequency spectrum and the second frequency spectrum.

7. The non-transitory computer-readable storage medium according to claim 1, wherein the existence of the inclusion relationship indicates that the second measured values contain a combination of the component of the first measured values and other components.

8. The non-transitory computer-readable storage medium according to claim 1, wherein the plurality of periods have an identical duration.

9. A determination method comprising:
obtaining, by a processor, a first time-series data set indicating first measured values obtained by a first device during a plurality of periods including a first period and a second period and a second time-series data set indicating second measured values obtained by a second device during the plurality of periods;
performing, by the processor, first alignment to convert positions in a time domain of first measured values belonging to the second period, based on first measured values belonging to the first period;
performing, by the processor, second alignment to convert positions in the time domain of second measured values belonging to the second period, based on a correspondence relationship between positions before and after conversion of the first alignment;
performing, by the processor, correlation analysis between a third time-series data set obtained by converting the first time-series data set using the first alignment and a fourth time-series data set obtained by converting the second time-series data set using the second alignment; and
determining, by the processor, existence or absence of an inclusion relationship, based on a result of the correlation analysis, the inclusion relationship indicating that the second measured values contain a component of the first measured values.

10. A determination apparatus comprising:
a memory that stores therein a first time-series data set indicating first measured values obtained by a first device during a plurality of periods including a first period and a second period and a second time-series data set indicating second measured values obtained by a second device during the plurality of periods; and
a processor that
performs first alignment to convert positions in a time domain of first measured values belonging to the second period, based on first measured values belonging to the first period,
performs second alignment to convert positions in the time domain of second measured values belonging to the second period, based on a correspondence relationship between positions before and after conversion of the first alignment, performs correlation analysis between a third time-series data set obtained by converting the first time-series data set using the first alignment and a fourth time-series data set obtained by converting the second time-series data set using the second alignment, and determines existence or absence of an inclusion relationship, based on a result of the correlation analysis, the inclusion relationship indicating that the second measured values contain a component of the first measured values.

* * * * *